(12) United States Patent
Allerton et al.

(10) Patent No.: US 6,784,185 B2
(45) Date of Patent: Aug. 31, 2004

(54) PHARMACEUTICALLY ACTIVE COMPOUNDS

(75) Inventors: Charlotte Moira Norfor Allerton, Sandwich (GB); Christopher Gordon Barber, Sandwich (GB); Mark Ian Kemp, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/098,900

(22) Filed: Mar. 14, 2002

(65) Prior Publication Data

US 2002/0198223 A1 Dec. 26, 2002

Related U.S. Application Data

(60) Provisional application No. 60/291,374, filed on May 16, 2001.

(30) Foreign Application Priority Data

Mar. 16, 2001 (GB) .............................................. 0106561
Mar. 16, 2001 (GB) .............................................. 0106651

(51) Int. Cl.[7] .................... C07D 487/04; A61K 31/519; A61P 15/12
(52) U.S. Cl. ..................... 514/262.1; 544/262
(58) Field of Search ........................ 544/262; 514/262.1

(56) References Cited

FOREIGN PATENT DOCUMENTS

| EP | 0526004 | 2/1993 |
|---|---|---|
| WO | WO9428902 | 12/1994 |
| WO | WO0127112 | 4/2001 |

OTHER PUBLICATIONS

XP–000872495, Estrade, Marielle, et al., Effect of a cGMP–specific phosphodiesterase inhibitor on retinal function, European Journal of Pharmacology, vol. 352, No. 2/3, 1998, pp. 157–163.

*Primary Examiner*—Mark L. Berch
*Assistant Examiner*—Kahsay Habte
(74) *Attorney, Agent, or Firm*—Peter C. Richardson; Gregg C. Benson; A. Dean Olson

(57) ABSTRACT

Compounds of general formula I:

I or pharmaceutically or veterinarily acceptable salts, solvates, polymorphs or pro-drugs thereof wherein:
wherein $R^1$, $R^2$, $R^3$, $R^4$, X and A have the meanings given herein which are useful in the curative and prophylactic treatment of a medical condition for which inhibition of a cyclic guanosine 3',5'-monophosphate phosphodiesterase (e.g. cGMP PDE5) is desired.

7 Claims, No Drawings

PHARMACEUTICALLY ACTIVE COMPOUNDS

This application claims priority from U.K. Application 0106651.3 filed Mar. 16, 2001; U.K. Application 0106561.4 filed Mar. 16, 2001; and U.S. Provisional Application 60/291,374 filed May 16, 2001.

FIELD OF THE INVENTION

This invention relates to pharmaceutically useful compounds, in particular compounds which are useful in the inhibition of cyclic guanosine 3',5'-monophosphate phosphodiesterases (cGMP PDEs), such as type 5 cyclic guanosine 3',5'-monophosphate phosphodiesterases (cGMP PDE5). The compounds therefore have utility in a variety of therapeutic areas, including male erectile dysfunction (MED).

International patent application WO 01/27112 discloses the use of certain pyrazolo[4,3-d]pyrimidinone compounds in the treatment of a variety of conditions and in particular MED.

The present application provides further pyrazolo[4,3-d]pyrimidinone compounds.

DISCLOSURE OF THE INVENTION

According to the present invention, there are provided compounds of general formula I:

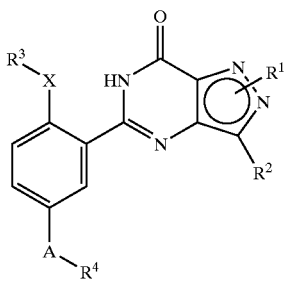

or pharmaceutically or veterinarily acceptable salts, solvates, polymorphs or pro-drugs thereof wherein:

A represents C(O) or CH(OH);

X represents O or $NR^5$;

$R^1$, $R^3$, $R^4$ and $R^5$ independently represent H, $C_1$–$C_6$ alkyl, Het, $C_1$–$C_6$ alkylHet, aryl or $C_1$–$C_6$ alkylaryl (which latter five groups may all be optionally substituted and/or terminated with one or more substituents selected from halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl wherein said latter five substituent and/or terminal groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $S_2R^{17}$; or when X represents $NR^5$ then $R^3$ and $R^5$ together with the nitrogen atom to which they are bound can form a heterocyclic ring which is optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $S_2R^{17}$;

$R^2$ represents H, halo, cyano, nitro, $OR^6$, $OC(O)R^6$, $C(O)R^6$, $C(O)OR^6$, $NR^6C(O)NR^7R^8$, $NR^6C(O)OR^6$, $C(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl (which latter five groups may all be optionally substituted and/or terminated with one or more substituents selected from halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl wherein said latter five substituent and/or terminal groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$);

$R^6$ represents H, $C_1$–$C_6$ alkyl, Het, $C_1$–$C_6$ alkylHet, aryl or $C_1$–$C_6$ alkylaryl (which latter five groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$);

$R^7$ and $R^8$ independently represent H, $C_1$–$C_6$ alkyl, Het, $C_1$–$C_6$ alkylHet, aryl or $C_1$–$C_6$ alkylaryl (which latter five groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$); or $R^7$ and $R^8$ together with the nitrogen atom to which they are bound can form a heterocyclic ring;

$R^9$ and $R^{10}$ independently represent H, $C(O)R^6$, $SO_2R^{11}$, $C_1$–$C_6$ alkyl, Het, $C_1$–$C_6$ alkylHet, aryl or $C_1$–$C_6$ alkylaryl (which latter five groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$ $SO_2NR^{15}R^{16}$, $SO_2R^{17}$); or $R^9$ and $R^{10}$ together with the nitrogen atom to which they are bound can form a heterocyclic ring;

wherein when $R^7$ and $R^8$, or $R^9$ and $R^{10}$ together with the nitrogen atom to which they are bound form a heterocyclic ring, said heterocyclic ring is optionally substituted and/or terminated with one or more substituents selected from: halo, cyano, nitro, $OR^{12}$, $OC(O)R^{12}$, $C(O)R^{12}$, $C(O)OR^{12}$, NR $C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^{11}$ represents a $C_1$–$C_6$ alkyl, Het, $C_1$–$C_6$ alkylHet, aryl or $C_1$–$C_6$ alkylaryl group is optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

R represents H or $C_1$–$C_6$ alkyl;

$R^{13}$ and $R^{14}$ independently represent H or $C_1$–$C_6$ alkyl; or $R^{13}$ and $R^{14}$ together with the nitrogen atom to which they are bound can form a heterocyclic ring;

$R^{15}$ and $R^{16}$ independently represent H, $C(O)R^{12}$, $SO_2R^{17}$ or $C_1$–$C_6$ alkyl; or $R^{15}$ and $R^{16}$ together with the nitrogen atom to which they are bound can form a heterocyclic ring;

$R^{17}$ represents $C_1$–$C_6$ alkyl;

Het represents an optionally substituted four- to twelve-membered heterocyclic group, which group contains one or more heteroatoms selected from nitrogen, oxygen, sulpur and mixtures thereof;

with the proviso that when X represents O and $R^1$ represents H, $C_1$–$C_3$ alkyl optionally substituted with fluoro or $C_3$–$C_5$ cycloalkyl then $R^2$ does not represent H, $C_1$–$C_6$ alkyl optionally substituted with one or more fluoro substituents or with $C_3$–$C_6$ cycloalkyl; or $R^3$ does not represent $C_1$–$C_6$ alkyl optionally substituted with one or more fluoro substituents or with $C_3$–$C_6$ cycloalkyl; $C_3$–$C_5$ cycloalkyl; $C_3$–$C_6$ alkenyl; or $C_3$–$C_6$ alkynyl; or $R_4$ does not represent $C_1$–$C_4$ alkyl optionally substituted with OH, $NR^9R^{10}$, CN, $CONR^9R^{10}$, $SO_2NR^9R^{10}$ or $CO_2R^6$ wherein $R^6$ is H or $C_1$–$C_4$ alkyl and $R^9$ and $R^{10}$ are each independently H or $C_1$–$C_4$ alkyl, or together with the nitrogen atom to which they are attached form a pyrrolidinyl, piperidino, morpholino, 4-substituted piperizinyl or imidazolyl group wherein said group is optionally substituted with $C_1$–$C_4$ alkyl or OH; $C_2$–$C_4$ alkenyl optionally substitued with CN, $CONR^9R^{10}$ or $CO_2R^6$; $C_2$–$C_4$ alkanoyl optionally substituted with $NR^9R^{10}$; ($C_2$–$C_4$)OH optionally substitued with $NR^9R^{10}$; ($C_2$–$C_3$) alkoxy($C_1$–$C_2$)alkyl optionally substituted with OH or $NR^9R^{10}$.

which compounds are referred to together hereinafter as "the compounds of the invention".

The term "aryl", when used herein, includes six- to ten-membered carbocyclic aromatic groups, such as phenyl and naphthyl.

The term "Het", when used herein, includes four- to twelve-membered, preferably four- to ten-membered, ring systems, which rings contain one or more heteroatoms selected from nitrogen, oxygen, sulfur and mixtures thereof, and which rings may contain one or more double bonds or be non-aromatic, partly aromatic or wholly aromatic in character. The ring systems may be monocyclic, bicyclic or fused. The term thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, tetrazolyl, oxatriazolyl, thiatriazolyl, pyridazinyl, morpholinyl, pyrimidinyl, pyrazinyl, pyridinyl, quinolinyl, isoquinolinyl, piperidinyl, pyrazolyl, imidazopyridinyl and piperazinyl. Substitution at Het may be at a carbon atom of the Het ring or, where appropriate, at one or more of the heteroatoms.

"Het" groups may also be in the form of an N-oxide.

The heterocyclic ring that $R^3$ and $R^5$, $R^7$ and $R^8$, $R^9$ and $R^{10}$, $R^{13}$ and $R^{14}$ or $R^{15}$ and $R^{16}$ (together with the nitrogen atom to which they are bound) may represent may be any heterocyclic ring that contains at least one nitrogen atom, and which ring forms a stable structure when attached to the remainder of the molecule via the essential nitrogen atom (which, for the avoidance of doubt, is the atom to which $R^3$ and $R^5$, $R^7$ and $R^8$, $R^9$ and $R^{10}$, $R^{13}$ and $R^{14}$ or $R^{15}$ and $R^{16}$ are attached). In this respect, heterocyclic rings that $R^3$ and $R^5$, $R^7$ and $R^8$, $R^9$ and $R^{10}$, $R^{13}$ and $R^{14}$ or $R^{15}$ and $R^{16}$ (together with the nitrogen atom to which they are bound) may represent include four- to twelve-membered, preferably four- to ten-membered, ring systems, which rings contain at least one nitrogen atom and optionally contain one or more further heteroatoms selected from nitrogen, oxygen and/or sulfur, and which rings may contain one or more double bonds or be non-aromatic, partly aromatic or wholly aromatic in character. The term thus includes groups such as azetidinyl, pyrrolidinyl, imidazolyl, indolyl, triazolyl, tetrazolyl, morpholinyl, piperidinyl, pyrazolyl and piperazinyl.

The term "$C_1$–$C_6$ alkyl" (which includes the alkyl part of alkylHet and alkylaryl groups), when used herein, includes methyl, ethyl, propyl, butyl, pentyl and hexyl groups. Unless otherwise specified, alkyl groups may, when there is a sufficient number of carbon atoms, be linear or branched, be saturated or unsaturated or be cyclic, acyclic or part cyclic/acyclic. Preferred $C_1$–$C_6$ alkyl groups for use herein are $C_1$–$C_3$ alkyl groups. The terms "$C_2$–$C_6$ alkenyl" and "$C_2$–$C_6$ alkynyl", when used herein, include $C_2$–$C_6$ groups having one or more double or triple carbon—carbon bonds, respectively. Otherwise, the terms "$C_2$–$C_6$ alkenyl" and "$C_2$–$C_6$ alkynyl" are defined in the same way as the term "$C_1$–$C_6$ alkyl". Similarly, the term "$C_1$–$C_6$ alkylene", when used herein, includes $C_1$–$C_6$ groups which can be bonded at two places on the group and is otherwise defined in the same way as "$C_1$–$C_6$ alkyl". The term "acyl" includes C(O)—($C_1$–$C_6$) alkyl.

Substituted alkylHet and alkylaryl as defined hereinbefore may have substituents on the ring and/or on the alkyl chain.

Halo groups with which the above-mentioned groups may be substituted or terminated include fluoro, chloro, bromo and iodo.

Compounds of general formula (I) can be represented by formulae IA and IB:

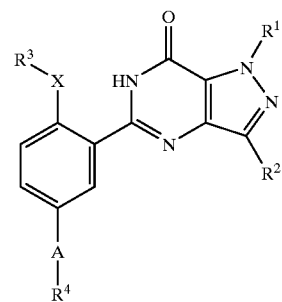

IA

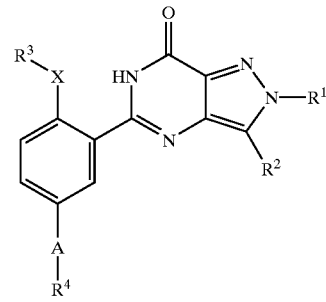

IB wherein $R^1$, $R^2$, $R^3$, $R^4$, A and X are as defined hereinbefore.

A preferred group of compounds according to a further aspect of the invention, are compounds of formulae IA or IB as hereinbefore defined, wherein:

X represents O;

A represents C(O) or CH(OH);

$R^1$ represents $C_1$–$C_6$ alkyl substituted and/or terminated with $OR^6$, $C(O)OR^6$, $C(O)NR^9R^{10}$ or $NR^9R^{10}$ wherein said latter four groups are optionally substituted and/or terminated as defined hereinbefore; or $R^1$ represents Het, $C_1$–$C_6$ alkylHet, aryl or $C_1$–$C_6$ alkylaryl optionally substituted and/or terminated with one or more substituents selected from halo, $C_1$–$C_6$ alkyl, $OR^6$, C(O) $OR^6$, $C(O)NR^9R^{10}$ and $NR^9R^{10}$ wherein said latter five groups are optionally substituted and/or terminated as defined hereinbefore;

R² and R³ independently represent $C_1$–$C_6$ alkyl, Het, $C_1$–$C_6$ alkylHet, aryl or $C_1$–$C_6$ alkylaryl optionally substituted and/or terminated with one or more substituents selected from halo, $OR^6$, $C(O)OR^6$ and $NR^9R^{10}$ wherein said latter three groups are optionally substituted and/or terminated as defined hereinbefore;

R⁴ represents $C_1$–$C_6$ alkyl, Het, $C_1$–$C_6$ alkylHet, aryl or $C_1$–$C_6$ alkylaryl optionally substituted and/or terminated with one or more substituents selected from halo and $OR^6$ wherein said $OR^6$ group is optionally substituted and/or terminated as defined hereinbefore;

wherein $R^6$, $R^9$ and $R^{10}$ are as hereinbefore defined.

A highly preferred group of compounds herein are those wherein:

A represents C(O) or CH(OH);

X represents O;

R¹ represents $C_1$–$C_6$ alkyl or $C_1$–$C_6$ alkylaryl wherein both groups are substituted and/or terminated with one or more substitutents selected from halo, $NR^9R^{10}$, $C(O)OR^6$ or $C(O)NR^9R^{10}$, or R¹ represents Het or $C_1$–$C_6$ alkylHet wherein both groups are optionally substituted and/or terminated with one or more substituent groups selected from halo, $OR^6$, $C_1$–$C_6$ alkyl and $NR^9R^{10}$;

R² represents $C_1$–$C_6$ alkyl optionally substituted and/or terminated with one or more substituent groups selected from halo and $OR^6$; or R² represents aryl or Het optionally substituted and/or terminated with one or more substituent groups selected from halo, $OR^6$ and $NR^9R^{10}$;

R³ represents $C_1$–$C_6$ alkyl, Het, $C_1$–$C_6$ alkylHet, aryl or $C_1$–$C_6$ alkylaryl optionally substituted and/or terminated with one or more substituents selected from halo and $OR^6$;

R⁴ represents $C_1$–$C_6$ alkyl optionally substituted and/or terminated with one or more substituents selected from halo and $OR^6$;

wherein $R^6$, $R^9$ and $R^{10}$ are as hereinbefore defined.

A further preferred group of compounds are those wherein:

A represents C(O) and X represents O;

R¹ represents $C_1$–$C_6$ alkyl optionally substituted and/or terminated with one or more substituent groups selected from $OR^6$, $C(O)OR^6$ and $C(O)NR^9R^{10}$; or R¹ represents Het or $C_1$–$C_6$ alkylHet optionally substituted and/or terminated with one or more substituent groups selected from $C_1$–$C_6$ alkyl, $OR^6$, $C(O)OR^6$ and $C(O)NR^9R^{10}$;

R² represents $C_1$–$C_6$ alkyl optionally substituted and/or terminated with one or more substituent groups selected from halo and $OR^6$;

R³ represents $C_1$–$C_6$ alkyl optionally substituted and/or terminated with one or more substituents selected from halo and $OR^6$;

R⁴ represents $C_1$–$C_6$ alkyl optionally substituted and/or terminated with one or more substituents selected from halo and $OR^6$;

wherein $R^6$, $R^9$ and $R^{10}$ are as hereinbefore defined.

An additional preferred group of compounds are those wherein:

A represents C(O) and X represents O;

R¹ represents $C_1$–$C_4$ alkyl, an azetidinyl group substituted and/or terminated with one or more substituent groups selected from $C_3$–$C_4$ alkyl, $OR^6$, $C(O)OR^6$ and $C(O)NR^9R^{10}$; or R¹ represents a ($C_1$–$C_6$)pyridinyl group which may be optionally substuted with one or more substituent groups selected from $C_3$–$C_4$ alkyl, $OR^6$, $C(O)OR^6$ and $C(O)NR^9R^{10}$;

R² represents $C_1$–$C_3$ alkyl optionally substituted and/or terminated with one or more substituent groups selected from halo and $OR^6$;

R³ represents $C_1$–$C_4$ alkyl optionally substituted and/or terminated with one or more substituents selected from halo and OR R⁴ represents $C_1$–$C_3$ alkyl optionally substituted and/or terminated with one or more substituents selected from halo and $OR^6$;

wherein $R^6$ is H or a $C_1$–$C_4$ alkyl group and wherein $R^9$ and $R^{10}$ are independently selected from methyl or ethyl groups.

An especially preferred group of compounds are those wherein:

A represents C(O) and X represents O;

R¹ represents $C_2$–$C_3$ alkyl group substituted and/or terminated with one or more substituent groups selected from $OR^6$ or $C(O)OR^6$;

R² represents $C_2$–$C_3$ alkyl, and is preferably ethyl, optionally substituted and/or terminated with one or more substituent groups selected from halo and $OR^6$;

R³ represents $C_3$–$C_4$ alkyl, and is preferably propyl, optionally substituted and/or terminated with one or more substituents selected from halo and $OR^6$;

R⁴ represents $C_1$–$C_2$ alkyl, and is preferably ethyl, optionally substituted and/or terminated with one or more substituents selected from halo and $OR^6$;

wherein $R^6$ is H or a $C_2$–$C_4$ alkyl group.

Especially preferred herein are compounds of formula I as described in the Examples section herein and in particular:

5-(5-Acetyl-2-butoxyphenyl)-2-(1-Cyclobutyl-3-azetidinyl)-3-ethyl-2,6-dihydro-7H-pyrazolo[4,3-d]pyrimidin-7-one;

tert-Butyl-5-[(5-acetyl-2-propoxyphenyl)-3-ethyl-7-oxo-6,7-dihydro-1H-pyrazolo[4,3-d]pyrimid in-1-yl]-acetate;

tert-Butyl-5-[(5-acetyl-2-propoxyphenyl)-3-ethyl-7-oxo-6,7-dihydro-2H-pyrazolo[4,3-d]pyrimidin-2-yl]-acetate;

tert-Butyl-3-[(5-acetyl-2-propoxyphenyl)-3-ethyl-7-oxo-6,7-dihydro-1H-pyrazolo[4,3-d]pyrimidin-1-yl]-2-methylpropanoate;

Ethyl-2-[5-(5-acetyl-2-propoxyphenyl)-3-ethyl-7-oxo-6,7-dihydro-2H-pyrazolo[4,3-d] pyrimidin-2-yl]propanoate;

Methyl-4-[5-(5-acetyl-2-propoxyphenyl)-3-ethyl-7-oxo-6,7-dihydro-1H-pyrazolo[4,3-d]pyrimidin-1-yl]-butanoate;

Methyl-4-[5-(5-acetyl-2-propoxyphenyl)-3-ethyl-7-oxo-6,7-dihydro-2H-pyrazolo[4,3-d]pyrimid in-1-yl]-butanoate;

4-[5-(5-Acetyl-2-propoxyphenyl)-3-ethyl-7-oxo-6,7-dihydro-1H-pyrazolo[4,3-d pyrimidin-1-yl]butanoic acid;

4-[5-(5-Acetyl-2-propoxyphenyl)-3-ethyl-7-oxo-6,7-dihydro-2H-pyrazolo[4,3-d]pyrimidin-2-yl]butanoic acid;

2-[5-(5-Acetyl-2-propoxyphenyl)-3-ethyl-7-oxo-6,7-dihydro-2H-pyrazolo[4,3-d]pyrimidin-2-yl]-N,N-dimethylacetamide and pharmaceutically acceptable salts, solvates and polymorphs thereof.

The present invention additionally provides compounds of general formula I:

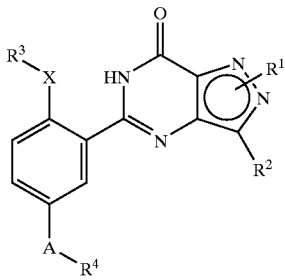

or pharmaceutically or veterinarily acceptable salts, solvates, polymorphs or pro-drugs thereof wherein:

A represents C(O) or CH(OH);

X represents O or $NR^5$;

$R^1$, $R^3$, $R^4$ and $R^5$ independently represent H, $C_1$–$C_6$ alkyl, Het, $C_1$–$C_6$ alkylHet, aryl or $C_1$–$C_6$ alkylaryl (which latter five groups may all be optionally substituted and/or terminated with one or more substituents selected from halo, cyano, nitro, $OR^6$, $OC(O)R^6$, $C(O)R$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{10}$, $C_1$–$C_6$ alkyl, Het, $C_1$–$C_6$ alkylHet, aryl or $C_1$–$C_6$ alkylaryl wherein said latter five substituent and/or terminal groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$); or $R^3$ and $R^5$ together with the nitrogen atom to which they are bound can form a heterocyclic ring which is optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^2$ represents H, halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{11}$, $SO_2R^{11}$, $C_1$–$C_6$ alkyl, Het, $C_1$–$C_6$ alkylHet, aryl or $C_1$–$C_6$ alkylaryl (which latter five groups may all be optionally substituted and/or terminated with one or more substituents selected from halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl wherein said latter five substituent and/or terminal groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$);

$R^6$ represents H, $C_1$–$C_6$ alkyl, Het, $C_1$–$C_6$ alkylHet, aryl or $C_1$–$C_6$ alkylaryl (which latter five groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$);

$R^7$ and $R^8$ independently represent H, $C_1$–$C_6$ alkyl, Het, $C_1$–$C_6$ alkylHet, aryl or $C_1$–$C_6$ alkylaryl (which latter five groups are all optionally substituted and/or terminated with one or more substituents selected from halo, cyano, nitro, $OR^{12}$ $OC(O)R^{12}$, $C(O)R^{12}$, $C(O)OR^{12}$, $NR^{12}(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$); or $R^7$ and $R^8$ together with the nitrogen atom to which they are bound can form a heterocyclic ring;

$R^9$ and $R^{10}$ independently represent H, $C(O)R^6$, $SO_2R^{11}$, $C_1$–$C_6$ alkyl, Het, $C_1$–$C_6$ alkylHet, aryl or $C_1$–$C_6$ alkylaryl (which latter five groups are all optionally substituted and/or terminated with one or more substituents selected from halo, cyano, nitro, $OR^{12}$, $OC(O)R^{12}$, $N(O)R^{12}$, $C(O)OR^{12}$, $NR^{12}C(O)NR^{13}R^{14}$, $NR^{12}(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$); or $R^9$ and $R^{10}$ together with the nitrogen atom to which they are bound can form a heterocyclic ring;

$R^{11}$ represents a $C_1$–$C_6$ alkyl, Het, $C_1$–$C_6$ alkylHet, aryl or $C_1$–$C_6$ alkylaryl group is optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^{12}$ represents H or $C_1$–$C_6$ alkyl;

$R^{13}$ and $R^{14}$ independently represent H or $C_1$–$C_6$ alkyl; or $R^{13}$ and $R^{14}$ together with the nitrogen atom to which they are bound can form a heterocyclic ring;

$R^{15}$ and $R^{16}$ independently represent H, $C(O)R^{12}$, $SO_2R^{17}$ or $C_1$–$C_6$ alkyl; or $R^{15}$ and $R^{16}$ together with the nitrogen atom to which they are bound can form a heterocyclic ring;

wherein when $R^7$ and $R^8$, or $R^9$ and $R^{10}$ together with the nitrogen atom to which they are bound form a heterocyclic ring, said heterocyclic ring is optionally substituted and/or terminated with one or more substituents selected from: halo, cyano, nitro, $OR^{12}$, $OC(O)R^{12}$, $C(O)R^{12}$, $C(O)OR^{12}$, $NR^{12}C(O)NR^{13}R^{14}$, $NR^{12}(O)OR^{12}$, $OC(O)NR^{13}R^{14}$, $C(O)NR^{15}R^{16}$, $NR^{15}R^{16}$ $SO_2NR^{15}R^{16}$, $SO_2R^{17}$;

$R^{17}$ represents $C_1$–$C_6$ alkyl;

Het represents an optionally substituted four- to twelve-membered heterocyclic group, which group contains one or more heteroatoms selected from nitrogen, oxygen, sulphur and mixtures thereof;

with the proviso that when X represents O then $R^1$ does not represent H, unsubstituted $C_1$–$C_6$ alkyl or $C_1$–$C_6$ alkyl substituted and/or terminated by one or more halo substituents.

The compounds of formula 1, and their pharmaceutically acceptable salts, have the advantage that they are inhibitors of the cGMP PDE5 enzyme, they have desirable potency, they demonstate desirable selectivity or have other more desirable properties versus the compounds of the prior art For successful utility within the pharmaceutical industry it is desirable that an active material should have good physical chemical properties, such as for example solubility. In some cases compounds can exhibit desirable medicinal properties which cannot be translated directly into a suitable pharmaceutical composition because the active compound itself has unsatisfactory physical properties such as for example poor chemical or processing properties.

The highly preferred compounds herein demonstrate desirable solubility characteristics in conjunction with desirable pharmacological properties, potency and selectivity.

Compounds of general formulae (I), (IA) or (IB) are referred to herein after as "the compounds of the invention" or "the compounds".

The pharmaceutically or veterinarily acceptable salts of the compounds which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, Hi, sulphate or bisulphate, nitrate, phosphate or hydrogen phosphate, acetate, benzoate, succinate, saccarate, fumarate, maleate, lactate, citrate, tartrate, gluconate, camsylate, methanesulphonate, ethanesulphonate, benzenesulphonate, p-toluenesulphonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al, J. Pharm, Sci., 66, 1–19, 1977.

The pharmaceutically acceptable solvates of the compounds include the hydrates thereof.

Also included within the scope herein are various salts of the compounds and polymorphs thereof.

Where a compound contains one or more asymmetric carbon atoms it therefore exists in two or more stereoisomeric forms. Where a compound contains an alkenyl or alkenylene group, cis (E) and trans (Z) isomerism may also occur. The present invention includes the individual stereoisomers of the compound and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate. All stereoisomers of the compounds are included within the scope herein.

The compounds may exhibit tautomerism. All tautomeric forms of the compounds, and mixtures thereof, are included within the scope herein.

Also included within the scope of the application are radiolabelled derivatives of the compounds which are suitable for biological studies.

Preparation

The compounds may be prepared in accordance with the methods detailed in the example and preparations section herein after. More specifically, routes by which the compounds herein may be prepared are as illustrated in Schemes 1, 2, 3 and 4 below:

SCHEME 1

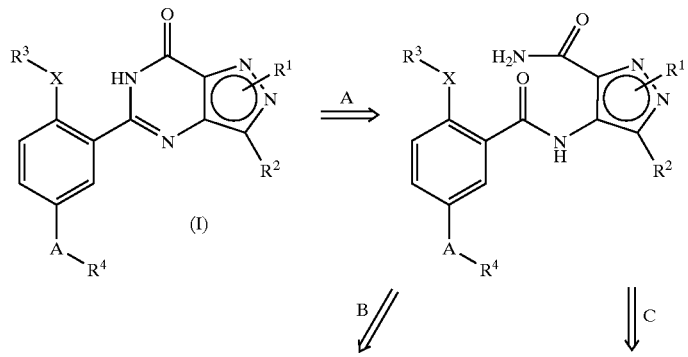

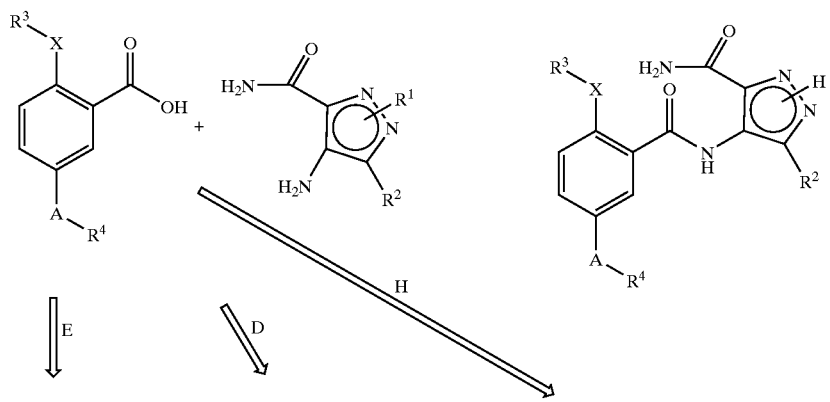

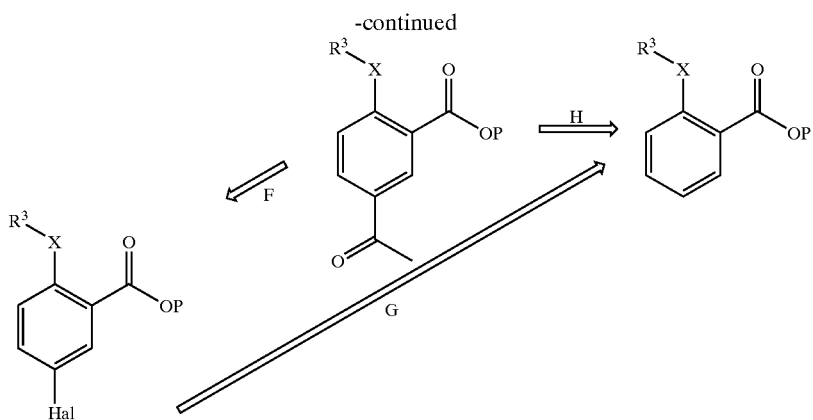

In the compounds of Scheme 1 $R^1$, $R^2$, $R^3$, $R^4$, A and X are as hereinbefore defined, P is either H or a protecting group, such as for example a methyl, ethyl or n-butyl group and Hal is a halogen, preferably Br or I. When P is an ester protecting group such group may be readily converted to the corresponding acid via suitable hydrolysis.

The compounds of Scheme 1 wherein A=CH(OH) can be prepared from the compounds of Scheme I wherein A=C(O) at any suitable stage in the route illustrated. Such transformation may be effected via use of a suitable reducing agent, preferably sodium borohydride in methanol. The reverse transformation can be effected via use of suitable oxidising conditions, such as for example magnesium dioxide oxidation.

The cyclodehydration reaction of Step A may be accomplished under basic, neutral or acidic conditions using known methods for pyrimidone ring formation. Preferably, the cyclisation is performed under either basic conditions such as by using an alkali metal salt of an alcohol or amine, such as sodium ethoxide, potassium tert-butoxide, cesium carbonate or potassium bis(trimethylsilyl)amide, in the presence of a suitable alcoholic solvent, such as ethanol, for example at reflux temperature and optionally elevated pressure (or, if performed in a sealed vessel, at greater than reflux temperature), or the cyclisation can be performed under acidic conditions using polyphosphoric acid. The skilled person will appreciate that, when X represents O and an alcohol is selected as solvent, an appropriate alcohol of formula $R^3OH$, may be used if it is intended to mitigate alkoxide exchange at the 2-position of the phenyl.

In general, Step A can be base mediated by using an alkali metal salt such as for example $Cs_2CO_3$, $K_2CO_3$, potassium bis(trimethylsilyl)amide (KHMDS) or $KO^tBu$, in an alcoholic solvent, preferably of formula $R^3OH$, or using a sterically hindered alcohol as solvent (e.g. 3-methyl-3-pentanol) at between about 70° C. to the reflux temperature of the selected solvent, for from 6 to about 30 hours, optionally at elevated pressure and optionally in the presence of a hydroxide scavenger, preferably $R^3OAc$.

Similarly, Step A can be acid mediated such as by treatment with either polyphosphoric acid at from about 130 to about 150° C. or with a Lewis acid, e.g. anhydrous zinc chloride at from about 200 to about 220° C.

Preferably Step A is carried out with from about 2 to 3 equivalents of $Cs_2CO_3$ or $KOBu^t$ in $R^3OH$, optionally in the presence of about 1 to 2 equivalents of $R^3OAc$, at the reflux temperature of the solvent, and optionally at elevated pressure, for between about 6 hours and about 5 days.

When $X-R^3$ is $-OR^3$ in the compound obtained from Step A, then it is possible to start Step A from a compound having either an $-OR^3$ or an $-OR^{3a}$ group wherein $-OR^{3a}$ represents $-OR^3$ or any alternative alkoxy group which is replaceable by $-OR^3$. Suitable $OR^{3a}$ groups include methoxy, ethoxy, n-propoxy, iso-propoxy, n-butoxy and any other alkoxy group capable of being exchanged for $-OR^3$ wherein $R^3$ is as defined hereinbefore. As defined herein $OR^{3a}$, for example when $-OR^3$ is ethoxy may either be ethoxy or be any alternative alkoxy group which is replaceable by ethoxy.

The coupling reaction of Step B may be achieved by conventional amide bond forming techniques which are well known to those skilled in the art. For example, an acyl halide (e.g. chloride) derivative of the starting benzoic acid with the pyrazole compound in the presence of an excess of a tertiary amine, such as triethylamine or pyridine, optionally in the presence of a suitable catalyst, such as 4-dimethylaminopyridine, in a suitable solvent such as dichloromethane or THF, at a temperature of about 0° C. to room temperature.

A variety of other amino acid coupling methodologies may be used to couple the benzoic acid compounds to the pyrazole compounds illustrated in Scheme 1. For example, the acid or a suitable salt thereof (e.g. sodium salt) may be activated with an appropriate activating reagent, e.g. a carbodiimide, such as 1,3-dicyclohexylcarbodiimide or 1-(3-dimethylaminopropyl)-3-ethylcarbodiimide hydrochloride optionally in the presence of 1-hydroxybenzotriazole hydrate and/or a catalyst such as 4-dimethylaminopyridine; a halotrisaminophosphonium salt such as bromo-tris(pyrrolidinyl)phosphonium hexafluorophosphate; a suitable pyridinium salt such as 2–Chloro-1-methyl pyridinium chloride; or another suitable coupling agent such as O-(7-azabenzotriazol-1-yl)-N,N,N',N'-tetramethyl-uronium hexafluorophosphate (HATU). Either type of coupling reaction may be conducted in a suitable solvent such as dichloromethane, tetrahydrofuran or N,N-dimethylformamide, optionally in the presence of a tertiary amine such as N-methylmorpholine or N-ethyldiisopropylamine (for example when either the pyrazole compound, or the activating agent is presented in the form of an acid addition salt), at from about 0° C. to about room temperature. Preferably, from about 1 to 2 molecular equivalents of the activating reagent and from 1 to 3 molecular equivalents of any tertiary amine present may be employed.

Alternatively, the carboxylic acid function of the benzoic acid compound may be activated using an excess of a suitable acid acceptor reagent such as N,N'-carbonyldiimidazole in an appropriate solvent, e.g. ethyl acetate, dichloromethane or butan-2-one, at from about room temperature to about 80° C., followed by reaction of the intermediate imidazolide with a pyrazole compound at from about 20° C. to about 90° C.

In a further variation, the final cyclised compound (of general formula (I), (IA) or (IB), as defined previously herein and as illustrated in the general process of Scheme 1), may be formed in a one-pot procedure by coupling the pyrazole compound and the acyl chloride derivative of the benzoic acid illustrated in Scheme 1 and by cyclising the resultant intermediate compound using the methods as described previously. The one-pot procedure may further involve an in-situ coupling and cyclisation reaction to form a compound of formula (I), (IA) or (IB). Preferably, pyridine may serve as an acid scavenger and as the solvent for the in-situ coupling and cyclisation reaction.

Typical conditions for Step B require the acid chloride (of the benzoic acid compound), the pyrazole compound and trimethylamine or pyridine at from 0° C. to about room temperature for up to about 16 hours. Alternative conditions for Step B require the acid, the pyrazolo compound, O-(7-azabenzotriazol-1-yl)-N,N,N'N'-tetramethyluronium hexafluor-phosphate (HATU reagent)/(PyBOP®) Benzotriazol-1-yloxytris(pyrrolidino) phosphonium hexafluorophosphate/(PYBrOP) bromo-tris-pyrrolidino-phosphonium hexafluorophosphate/Mukaiyama's reagent (2-Chloro-1-methylpyridinium iodide) or 1-(3-dimethylaminopropyl)-3-ethylcarbodiimide hydrochloride (WSCDI)/N,N'-dicyclohexylcarbodiimide (DCC) and (HOBT)/1-hydroxy-7-azabenzotriazole (HOAT), with an excess of N-methyl morpholine (NMM), or triethylamine, or Hünigs base in THF, dichloromethane or ethyl acetate, at room temperature for from about 1 to about 48 hrs.

Preferred conditions for Step B are using about 1 equivalent of the acid chloride and about 1 equivalent of the pyrazole with an excess (about 3 equivalents) of triethylamine in dichloromethane for about 3 hours at room temperature.

Step C is an alkylation reaction with $R^1L$, where L is a suitable leaving group, such as halo, tosylate, mesylate, in the presence of a base, optionally in the presence of a catalyst, in a solvent at between 0° C. and the reflux temperature of the solvent. Typical conditions utilise a slight excess of $R^1L$, a slight excess of base, such as $K_2CO_3$ or $Cs_2CO_3$, in DMF or MeCN, at between about 40° C. and about 100° C.

Preferred conditions for Step C use from about 1.2 to about 2 equivalents of $R^1L$, (wherein L is preferably Cl, I or mesylate or tosylate), and from about 1.2 to about 1.5 equivalents of $Cs_2CO_3$, in DMF at between about 50° C. and about 90° C. for from about 16 to about 34 hours.

In Step C the $R^1$ group may be a protected group as illustrated below:

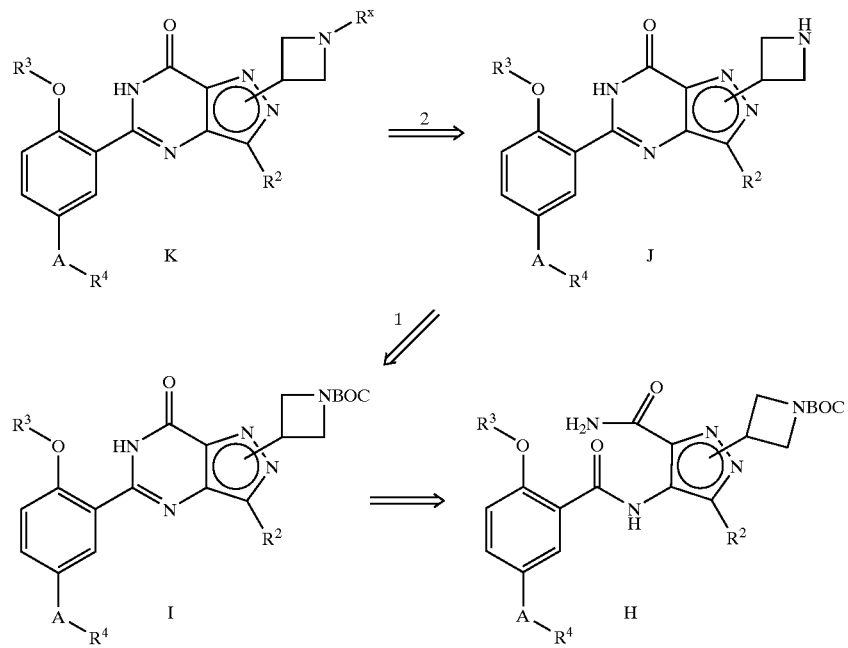

Step D provides functionalisation at a position alpha to the ketone substituent (at the 5' position on the phenyl ring). Such functionalisation of for example a methyl ketone to a substituted methyl ketone can occur at any step and in any route. Step D applies when A represents C=O and $R^4$ represents methylene substituted with groups defined hereinbefore. Using standard conditions to enable halogenation, preferably bromination, alpha- to the ketone to form alpha-halo ketones, or conditions to enable oxidation alpha- to the ketone where the resulting alpha-hydroxy group is converted to a leaving group. The halogen or oxygenated leaving group can then be displaced by a suitable nucleophile, e.g. primary or secondary amine.

Preferred conditions for step D are bromination using about 1.1 equivalent of N-bromosuccinimide, about 3 equivalents of triflic acid and dichloromethane. Alternatively, addition of a base will allow formation of the enolate, which can then be quenched on to a suitable electrophile (e.g. lower alkyl halide). Typical conditions for such transformation are form about 1.1 to about 2 equivalents of suitable base (e.g. LDA, NaH), from about 1.1 to about 2 equivalents of suitable electrophile (e.g. lower alkyl halides) in THF or ether followed by reaction with an $R^4L$ group wherein L is a suitable leaving group. Advantageously, during Step D ester hydrolysis can also occur thereby enabling acid coupling with the pyrazole amine following isolation of the acidic product.

These transformations can occur when P=H or protecting group (as detailed hereinbefore).

Step E introduces a functionalised ketone moiety into the phenyl compound. Conversion of Hal to A—$R^4$ can occur at any step in any of the routes. This can be achieved by any one of the routes outlined below:

(a) so-called "Heck" conditions (e.g. 2 eq. of a source of an acyl anion equivalent (such as butyl vinyl ether), 1.7 eq. of $Et_3N$ and catalytic amounts of $Pd(OAc)_2$ and $P(o\text{-tol})_3$, in MeCN at between room temperature and reflux). Performing a Heck reaction on an alkyl alkenyl ether (will give products where A represents C=O). Such reactions are not suitable when $R^4$ is aryl; or (b) so-called "Sonogashira" conditions (for example as described in *Synthesis* 1980, 8, 627, such as 1.5 to 5 eq. of a terminal alkyne and 0.024 to 0.03 eq. of $Pd(PPh_3)_2$ $Cl_2$/CuI, in $Et_3N$ and MeCN at between room temperature and 60° C.), followed by hydrolysis of the resultant alkyne (typical conditions 0.3 equiv. $HgSO_4$, $H_2SO_4$, acetone at reflux). Note, this procedure will give products where A represents C=O. Such reactions are not suitable when $R^4$ is aryl; or (c) Halogen/lithium exchange followed by quenching onto an acyl chloride (to give products where A represents C=O). Alternatively, the anion could be quenched onto an aldehyde to give products where A represents CH(OH). This alcohol could then be re-oxidised to the corresponding ketone by methods described hereinbefore. Preferred conditions for acyl chloride reaction: 1–2 equivalents of n-Butyl Lithium, 1–2 equivalents of $R^4COCl$, THF, at from about –78° C. to about room temperature. If for example $R^4COCl$ is $LCH_2COCl$ (where L is a leaving group as defined earlier), then once the above procedure has been performed the product can be further functionalised by displacement of L with a nucleophile (e.g. primary or secondary amine)

(d) Formation of Grignard or zincate through addition of magnesium or a zinc source (e.g. zinc, zinc chloride, Reike zinc), followed by quenching onto an acyl chloride (to give products where A represents C=O). Alternatively the Grignard or zinc reagent could be quenched onto an aldehyde to give products where A represents CH(OH). Again, the alcohol formed could be oxidised to give the required ketone as detailed hereinbefore.

(e) Carbonylation to yield a carboxylic acid, ester, or Weinreb amide. Preferred conditions: CO (50 psi), $Pd(OAc)_2$ (0.03 eq.), 1,1'-bis(diphenylphosphino)ferrocene (0.045 eq.), triethylamine (5 eq.), and suitable nucleophile (e.g. alcohol, amine) at from 40 to about 80° C. Alternatively the Weinreb amide can be synthesised from the carboxylic acid and the aldehyde could be synthesised from the ester or carboxylic acid. The acid chloride can be formed from the carboxylic acid. Preferred conditions to from acid chloride from acid: $(COCl)_2$ (1.2 eq.), DMF (drop), DCM. A nucleophile such as a Grignard reagent or zincate can then be reacted with the ester, Weinreb amide or acid chloride to yield products where A represents C=O. Alternatively, analogous reactions with the aldehyde would yield products where A represents CH(OH). Preferred conditions for addition of Grignard reagent into acid chloride: $R^4$ MgBr (1 eq.), $Fe(acac)_3$ (0.03 eq.), THF. Advantageously, during Step E "in-situ" hydrolysis of the ester protecting group can occur thereby enabling acid coupling with the pyrazole amine following isolation of the acidic product.

These transformations can occur when P=H or protecting group (as detailed hereinbefore).

Step F illustrates the formation of a methyl ketone from the appropriate halogenated phenyl compound. Conversion of Hal to C(O)Me can occur at any step in any of the routes, by the methods outlined in E(a) to (e) above.

Step G illustrates the halogenation of 2-alkoxy benzoates wherein Hal represents Cl, Br or I, preferably Br or I. Typical conditions for halogenation are N-iodosuccinimide (1 to 2 eq.), trifluoroacetic acid:trifluoroacetic anhydride (4:1 mixture as solvent) at temperatures between room temperature and reflux. Once halogenation has occurred the 2-alkoxy substituent can be exchanged with alternative alkoxy or amino substituents. This 2' exchange reaction can also occur at any subsequent step in the synthesis of the compounds of general formula (I). Typical conditions for 2' exchange with alternative alkoxy substituents are $Cs_2CO_3$ (2 to 4 eq.) or $KO^tBu$ (1 to 3 eq.) or KHMDS (2 to 5 eq.), ROH as solvent at temperatures between room temperature and reflux. Typical conditions for 2' exchange with amino substituents are copper sulphate (catalytic), R'R"NH$_2$ at temperatures between room temperature and reflux.

Step H provides for acylation at the C-5 position of the phenyl ring using Friedel Crafts reactions (to give products where A represents C=O). Typical conditions: $AlCl_3$ (2 to 10 eq.), RCOCl (1 to 3 eq.), DCM at 0° C. to reflux.

An alternative synthesis of the starting acid in reaction B (compound P), where A—$R^4$ is acetyl can be accomplished in two steps (reactions O and N) from a protected acid (compound Q) as illustrated below:

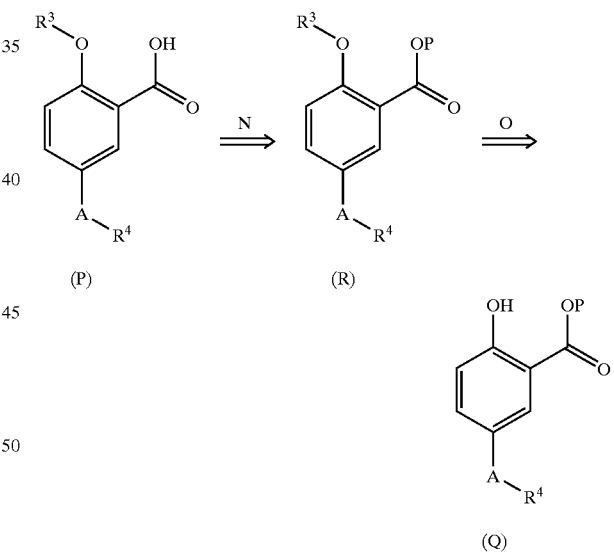

In Step N the protected acid R undergoes ester hydrolysis under standard conditions, typically using about 2 equivalents of sodium hydroxide in a dioxan: water mixture with a volume ratio of 10:1 at room temperature for about 18 hours.

In Step O the alkylation reaction (of the OH group) is typically accomplished by use of from about 4.5 to about 6 equivalents of $R^3L$ wherein L is a suitable leaving group, and wherein L is preferably 1, with about 3 to about 4.5 equivalents of a suitable base, such as $K_2CO_3$ in an appropriate solvent such as acetonitrile for 3 to 4 days at 60° C. to about 80° C.

Scheme 2 illustrates the preparation of the compounds via a process wherein the R¹ substituent is included as the final step.

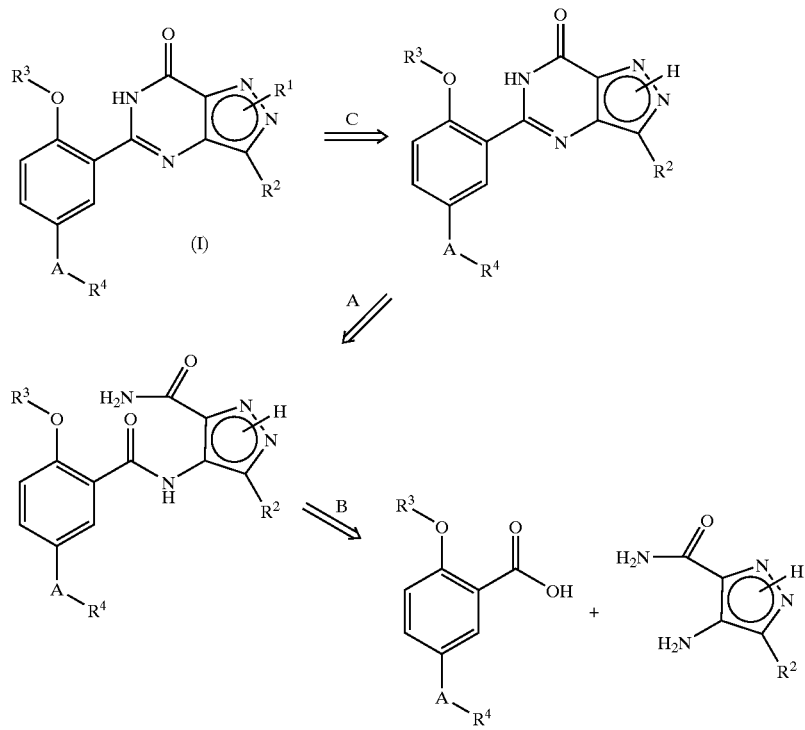

In Scheme 2, A, X, R¹, R², R³ and R⁴ are as hereinbefore defined.

Step C is an alkylation reaction with R¹L, where L is a suitable leaving group, such as halo, tosylate, mesylate, in the presence of a base, optionally in the presence of a catalyst, in a solvent at between 0 and 40° C. Typical conditions utilise an excess of R¹L, a slight excess of base, such as $K_2CO_3$ or $Cs_2CO_3$, in DMF or MeCN, at between about 0 and about 40° C.

Preferred conditions for step C use from about 1.0 to about 1.1 equivalents of R¹L, (wherein L is preferably Cl), and about 1.4 to about 1.6, more preferably about 1.5 equivalents of $Cs_2CO_3$, in DMF at room temperature from 24 to about 72 hours.

Steps A and B can be carried out using the conditions and reagents as detailed herein before in relation to Scheme 1.

Illustrated in Scheme 3 is a general process whereby, when R² may be added to the general structure.

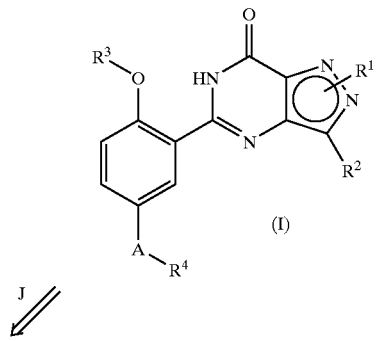

-continued

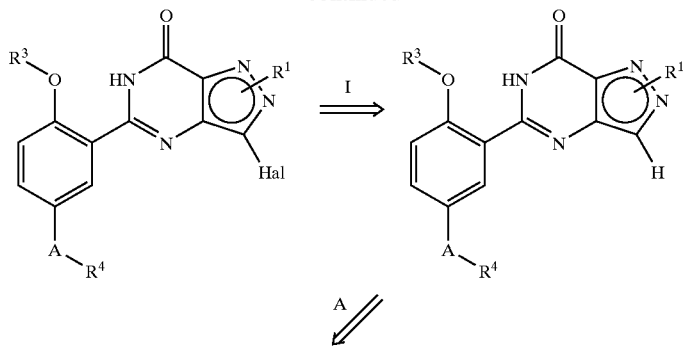

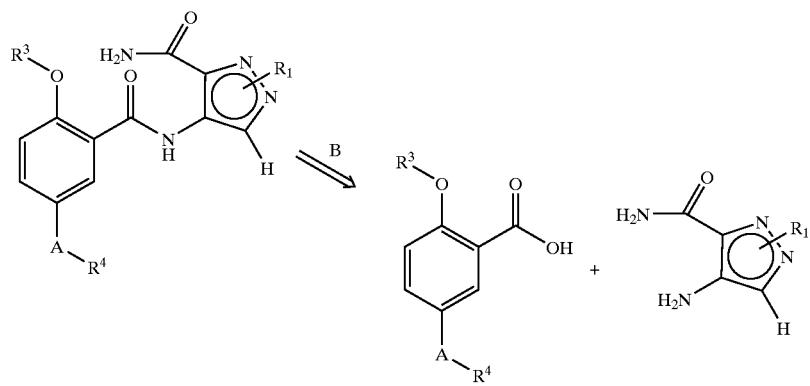

In Scheme 3, A, X, $R^1$, $R^2$, $R^3$ and $R^4$ are as hereinbefore defined and Hal is Cl, Br or I.

Step I provides for halogenation at the C-3 position on the pyrazole ring. In Step I, Hal represents Cl, Br or I in this instance and is preferably Br. Typical conditions for bromination are bromine (1.5 to 2 equiv.) and sodium acetate (1.5 to 2 equiv.) in a suitable solvent (e.g. acetic acid) at temperatures between room temperature and the reflux temperature of the solvent. Optionally, this halogenation step can be performed at other stages in the reactions sequence illustrated in Scheme 3 (i.e. before cyclisation or before coupling).

In Step J, wherein Hal=I, Pd coupling is used to introduce the $R^2$ group. Such reagents are applicable where $R^2$ is alkyl, alkylHet, Het, Aryl or alkylAryl (all optionally substituted as defined hereinbefore), as well as cyano, $C(O)R^6$ and $C(O)O R^6$ (wherein $R^6$ is as described hereinbefore) using coupling conditions such as are known to those skilled in the art.

(a) so-called "Suzuki" conditions (e.g. 1.2 eq. of boronic acid, 2 eq. of $K_2CO_3$ and 0.1 eq. of $Pd(PPh_3)_4$, refluxing in an approximately 4:1 mixture of dioxane:water, or 2.5 to 3 eq. of CsF, 0.05 to 0.1 eq. of $Pd_2(dba)_3$ and 0.01 to 0.04 eq of $P(o\text{-tol})_3$, refluxing in DME);

(b) so-called "Stille" conditions (e.g. 1.5 eq. of stannane, 10 eq. of LiCl, 0.15 eq. of CuI, and 0.1 eq. of $Pd(PPh_3)_4$, refluxing in dioxane, or 5 eq. of stannane, 3.6 eq. of $Et_3N$, $Pd_2(dba)$ and $P(o\text{-tol})_3$, refluxing in MeCN);

(c) so-called "Heck" conditions (e.g. 2 eq. of a source of an acyl anion equivalent (such as butyl vinyl ether), 1.7 eq. of $Et_3N$ and catalytic amounts of $Pd(OAc)_2$ and $P(o\text{-tol})_3$, in MeCN at between room temperature and reflux); or (d) so-called "Sonogashira" conditions (for example as described in Synthesis 1980, 8, 627, such as 1.5 to 5 eq. of a terminal alkyne and 0.024 to 0.03 eq. of $Pd(PPh_3)_2 Cl_2$/CuI, in $Et_3N$ and MeCN at between room temperature and 60° C.); or (e) carbonylation conditions such as reaction with an appropriate palladium catalyst system (e.g. palladium(II) acetate combined with 1,2-bis(diphenylphosphino)-propane (DPPP)) under an atmosphere of carbon monoxide (e.g. at a pressure of around 482.6 kPa (70 psi)) in the presence of an excess of an alcohol, an excess of a tertiary amine base (e.g. $Et_3N$), and optionally in the presence of a suitable solvent (e.g. dimethylsulfoxide).

The skilled chemist would appreciate that the steps described above can be carried out in any order, for example the conversion of Hal to $—AR^4$, optionally via $C(O)Me$, can take place either before or after coupling or before or after cyclisation.

Steps A and B are as hereinbefore detailed.

Scheme 4 illustrates a general process wherein compounds of formula (I) can be prepared from similar compounds wherein $R^1$ is introduced onto a protected pyrimidinone.

SCHEME 4

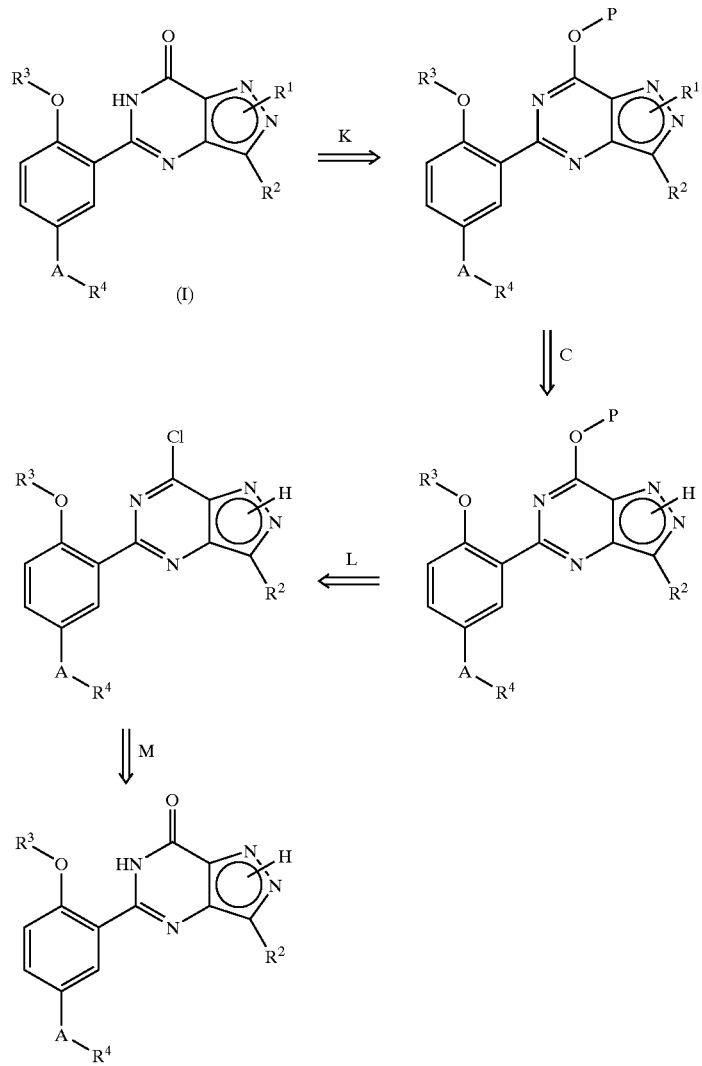

In Scheme 4, A, X, $R^1$, $R^2$, $R^3$ and $R^4$ are as hereinbefore defined.

Step K involves the removal of pyrimidinone protecting group wherein P is a hydroxy protecting group, preferably Me. Typical conditions for removing methyl are via use of 6M HCl at temperatures of between room temperature and about 70° C.

Step L introduces an alkoxy group onto the halogenated (chloroinated) pyrimidine ring. Typical conditions are to react the chloropyrimidine with POH (where P is defined as above) at between room and reflux temperature in the presence of a suitable base (e.g. potassium tert-butoxide).

Step M involves chlorination of pyrimidinone ring. Typical conditions are to react with a chlorinating agent (e.g. POCl₃) at between room and reflux temperature, optionally in a suitable solvent and optionally in the presence of from about 1 to about 2 equivalents of a suitable additive (e.g. N,N-dimethylformamide or N,N-dimethylaniline).

Protection/deprotection strategies as appropriate may be employed such as are known in the literature. Suitable protecting groups for use in accordance with the invention can be found in "Protecting Groups" edited by P. J. Kocienski, Thieme, New York, 1994; and "Protective Groups in Organic Synthesis" $2^{nd}$ edition, T. W. Greeene & P. G. M. Wutz, Wiley-Interscience (1991).

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula (I) may act as prodrugs of other compounds of formula (I).

All protected derivatives, and prodrugs, of compounds of formula (I) are included within the scope of the invention. Examples of suitable pro-drugs for the compounds of the present invention are described in Drugs of Today, Volume 19, Number 9, 1983, pp 499–538 and in Topics in Chemistry, Chapter 31, pp 306–316 and in "Design of Prodrugs" by H. Bundgaard, Elsevier, 1985, Chapter 1 (the disclosures in which documents are incorporated herein by reference).

It will further be appreciated by those skilled in the art, that certain moieties, known to those skilled in the art as "pro-moieties", for example as described by H. Bundgaard in "design of Prodrugs" (the disclosure in which document is incorporated herein by reference) may be placed on appropriate functionalities when such functionalities are present within compounds of formula (I).

Preferred prodrugs for compounds of formula (I) include: alcohols, esters, carbonate esters, hemi-esters, phosphate esters, nitro esters, sulfate esters, sulphoxides, amides, carbamates, azo-compounds, phosphamides, glycosides, ethers, acetals and ketals.

Pharmaceutically acceptable acid addition salts of the compounds which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound with the appropriate base. Both types of salt may be formed or interconverted using ion-exchange resin techniques.

The present application also includes all suitable isotopic variations of the compounds or pharmaceutically acceptable salts thereof. An isotopic variation of a compound or a pharmaceutically acceptable salt thereof is defined as one in which at least one atom is replaced by an atom having the same atomic number but an atomic mass different from the atomic mass usually found in nature. Examples of isotopes that can be incorporated into the compounds and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as 2 deuterium, i.e., H, may afford certain therapeutic advantages resulting from greater metabolic stability, for example, increased in vivo half-life or reduced dosage requirements and hence may be preferred in some circumstances. Isotopic variations of the compounds and pharmaceutically acceptable salts thereof of this invention can generally be prepared by conventional procedures such as by the illustrative methods or by the preparations described in the Examples and Preparations hereafter using appropriate isotopic variations of suitable reagents.

It will be appreciated by those skilled in the art that certain protected derivatives of the compounds, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds may act as prodrugs of other compounds.

All protected derivatives, and prodrugs, of the compounds are included within the scope.

The present invention additionally comprises the combination of a cGMP $PDE_5$ inhibitor compound as defined herein, wherein said combination can be administered by sequential, simultaneous or joint administration of a compound with:

(1) one or more naturally occurring or synthetic prostaglandins or esters thereof. Suitable prostaglandins for use herein include compounds such as alprostadil, prostaglandin $E_1$, prostaglandin $E_0$, 13, 14-dihydroprostaglandin $E_1$, prostaglandin $E_2$, eprostinol, natural synthetic and semi-synthetic prostaglandins and derivatives thereof including those described in U.S. Pat. No. 6,037,346 issued on Mar. 14, 2000 and incorporated herein by reference, $PGE_0$, $PGE_1$, $PGA_1$, $PGB_1$, $PGF_1$ α, 19-hydroxy $PGA_1$, 19-hydroxy—$PGB_1$, $PGE_2$, $PGB_2$, 19-hydroxy-$PGA_2$, 19-hydroxy-$PGB_2$, $PGE_3α$, carboprost tromethamine dinoprost, tromethamine, dinoprostone, lipo prost, gemeprost, metenoprost, sulprostune, tiaprost and moxisylate; and/or (2) one or more α-adrenergic receptor antagonist compounds also known as α-adrenoceptors or α-receptors or α-blockers. Suitable compounds for use herein include: the α-adrenergic receptors as described in PCT application WO99/30697 published on Jun. 14, 1998, the disclosures of which relating to α-adrenergic receptors are incorporated herein by reference and include, selective $α_1$-adrenoceptors or $α_2$-adrenoceptors and non-selective adrenoceptors, suitable $α_1$-adrenoceptors include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; α2-blockers from U.S. Pat. No. 6,037,346 [Mar. 14, 2000] dibenarnine, tolazoline, trimazosin and dibenarnine; α-adrenergic receptors as described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $α_2$-Adrenoceptors include: clonidine, papaverine, papaverine hydrochloride, optionally in the presence of a cariotonic agent such as pirxamine; and/or (3) one or more NO-donor (NO-agonist) compounds. Suitable NO-donor compounds for use herein include organic nitrates, such as mono- di or tri-nitrates or organic nitrate esters including glyceryl brinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy—L-arginine, amylnitrate, linsidomine, linsidomine chlorohydrate, (SIN-1) S-nitroso—N-cysteine, diazenium diolates,(NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075; and/or (4) one or more potassium channel openers. Suitable potassium channel openers for use herein include nicorandil, cromokalim, levcromakalim, lemakalim, pinacidil, cliazoxide, minoxidil, charybdotoxin, glyburide, 4-amini pyridine, $BaCl_2$; and/or (5) one or more dopaminergic agents, preferably apomorphine or a selective D2, D3 or D2/D3 agonist such as pramipexol and ropirinol (as claimed in WO 0023056), L-Dopa or carbi dopa, PNU 95666 (as claimed in WO 0040226); and/or (6) one or more vasodilator agents. Suitable vasodilator agents for use herein include nimodepine, pinacidil, cyclandelate, isoxsuprine, chloroprumazine, halo peridol, Rec 15/2739, trazodone; and/or (7) one or more thromboxane A2 agonists; and/or (8) one or more ergot alkoloids; Suitable ergot alkaloids are described in U.S. Pat. No. 6,037,346 issued on Mar. 14, 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride; and/or (9) one or more compounds which modulate the action of atrial natruretic factor (also known as atrial naturetic peptide), B and C type naturetic factors such as inhibitors or neutral endopeptidase; and/or

(10) one or more compounds which inhibit angiotensin-converting enzyme such as enapril, and one or more combined inhibitors of angiotensin-converting enzyme and neutral endopeptidase such as omapatrilat; and/or

(11) one or more angiotensin receptor antagonists such as losartan; and/or

(12) one or more substrates for NO-synthase, such as L-arginine; and/or

(13) one or more calcium channel blockers such as amlodipine; and/or

(14) one or more antagonists of endothelin receptors and inhibitors or endothelin-converting enzyme; and/or

(15) one or more cholesterol lowering agents such as statins (e.g. atorvastatin/Lipitor—trade mark) and fibrates; and/or

(16) one or more antiplatelet and antithrombotic agents, e.g. tPA, uPA, warfarin, hirudin and other thrombin inhibitors, heparin, thromboplastin activating factor inhibitors; and/or

(17) one or more insulin sensitising agents such as rezulin and hypoglycaemic agents such as glipizide; and/or

(18) one or more COX 2 inhibitors; and/or

(19) pregabalene; and/or

(20) gabapentene; and/or

(21) one or more acetylcholinesterase inhibitors such as donezipil; and/or

(22) one or more steroidal anti-inflammatory agents; and/or

(23) one or more estrogen agonists and/or estrogen antagonists, preferably raloxifene or lasofoxifene, (−)-cis-6-phenyl-5-[4-(2-pyrrolidin-1-yl-ethoxy)-phenyl]-5,6,7,8-tetrahydronaphthalene-2-ol and pharmaceutically acceptable salts thereof (compound A below) the preparation of which is detailed in WO 96/21656.

Compound A

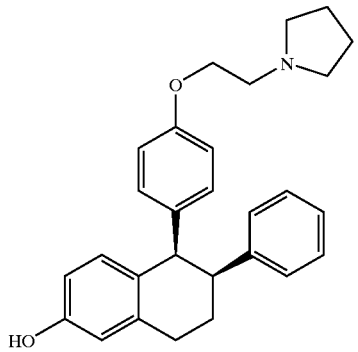

(24) one or more one or more of a further PDE inhibitor, more particularly a PDE 2, 4, 7 or 8 inhibitor, preferably PDE2 inhibitor, said inhibitors preferably having an IC50 against the respective enzyme of less than 100 nM; and/or

(25) one or more of an NPY (neuropeptide Y) inhibitor, more particularly NPY1 or NPY5 inhibitor, preferably NPY1 inhibitor, preferably said NPY inhibitors (including NPY Y1 and NPY Y5) having an IC50 of less than 100 nM, more preferably less than 50 nM, suitable NPY and in particular NPY1 inhibitor compounds are described in EP-A-1097718; and/or

(26) one or more of vasoactive intestinal peptide (VIP), VIP mimetic, more particularly mediated by one or more of the VIP receptor subtypes VPAC1, VPAC or PACAP (pituitary adenylate cyclase activating peptide), one or more of a VIP receptor agonist or a VIP analogue (eg Ro-125-1553) or a VIP fragment, one or more of a α-adrenoceptor antagonist with VIP combination (eg Invicorp, Aviptadil); and/or

(27) one or more of a melanocortin receptor agonist or modulator or melanocortin ehancer, such as melanotan II, PT-14, PT-141 or compounds claimed in WO-09964002, WO-00074679, WO-09955679, WO-00105401, WO-00058361, WO-00114879, WO-00113112, WO-09954358; and/or

(28) one or more of a serotonin receptor agonist, antagonist or modulator, more particularly agonists, antagonists or modulators for 5HT1A (including VML 670), 5HT2A, 5HT2C, 5HT3 and/or 5HT6 receptors, including those described in WO-09902159, WO-00002550 and/or WO-00028993; and/or

(29) one or more of a modulator of transporters for noradrenaline, dopamine and/or serotonin, such as bupropion, GW-320659; and/or

(30) one or more of a purinergic receptor agonist and/or modulator; and/or

(31) one or more of a neurokinin (NK) receptor antagonist, including those described in WO-09964008; and/or

(32) one or more of an opioid receptor agonist, antagonist or modulator, preferably agonists for the ORL-1 receptor; and/or

(33) one or more of an agonist or modulator for oxytocin/vasopressin receptors, preferably a selective oxytocin agonist or modulator; and/or

(34) one or more modulators of cannabinoid receptors; and/or

(35) one or more of an NEP inhibitor, preferably wherein said NEP is EC 3.4.24.11 and more preferably wherein said NEP inhibitor is a selective inhibitor for $EC_{3.4.24.11}$, more preferably a selective NEP inhibitor is a selective inhibitor for $EC_{3.4.24.11}$, which has an IC50 of less than 100 nM (e.g. ompatrilat, sampatrilat) suitable NEP inhibitor compounds are described in EP-A-1097719; and/or

(36) one or more compounds which inhibit angiotensin-converting enzyme such as enalapril, and one or more combined inhibitors of angiotensin-converting enzyme and neutral endopeptidase such as omapatrilat; and/or

(37) one or more tricyclic antidepressants, e.g. amitriptiline; and/or

(38) one or more non-steroidal anti-inflammatory agents; and/or

(39) one or more angiotensin-converting enzyme (ACE) inhibitors, e.g. quinapril; and/or

(40) one or more anti-depressants (such as clomipramine and SSRIs (such as paroxetine and sertaline).

wherein said combination can be in the form of co-administration, simultaneous administration, concurrent administration, or stepwise administration.

Medical Use

The compounds of the invention are useful because they possess pharmacological activity in animals, especially mammals, including humans. They are therefore indicated as pharmaceuticals, as well as for use as animal medicaments.

According to a further aspect of the invention there is provided the compounds of the invention for use as pharmaceuticals, and for use as animal medicaments.

In particular, compounds of the invention have been found to be potent and selective inhibitors of cGMP PDE5, such as cGMP PDE5, for example as demonstrated in the tests described below, and are thus useful in the treatment of medical conditions in humans, and in animals, in which cGMP PDEs, such as cGMP PDE5, are indicated, and in which inhibition of cGMP PDEs, such as cGMP PDE5, is desirable.

By the term "treatment", we include both therapeutic (curative), palliative or prophylactic treatment.

Thus, according to a further aspect of the invention there is provided the use of the compounds of the invention in the manufacture of a medicament for the treatment of a medical condition in which a cGMP PDE (e.g. cGMP PDE5) is indicated. There is further provided the use of the compounds of the invention in the manufacture of a medicament for the treatment of a medical condition in which inhibition of a cGMP PDE (e.g. cGMP PDE5) is desirable.

The compounds of the invention are thus expected to be useful for the curative, palliative or prophylactic treatment of mammalian sexual disorders. In particular, the compounds are of value in the treatment of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) as well as sexual dysfunction due to spinal cord injury or selective serotonin re-uptake inhibitor (SSRI) induced sexual dysfunction but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, diseases and conditions of the eye such as glaucoma, optic neuropathy, macular degeneration, elevated intra-occular pressure, retinal or arterial occulsion and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful, include pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof (e.g. gastroparesis), peripheral diabetic neuropathy, Alzheimer's disease, acute respiratory failure, psoriasis, skin necrosis, cancer, metastasis, baldness, nutcracker oesophagus, anal fissure, haemorrhoids, hypoxic vasoconstriction, hypoxic vasoconstriction, diabetes, type 2 diabetes mellitus, the insulin resistance syndrome, insulin resistance, impaired glucose tolerance, as well as the stabilisation of blood pressure during haemodialysis.

Particularly preferred conditions include MED and FSD.

Thus, the invention provides a method of treating or preventing a medical condition for which a cGMP PDE5 inhibitor is indicated, in an animal (e.g. a mammal, including a human being), which comprises administering a therapeutically effective amount of a compound of the invention to a mammal in need of such treatment.

Pharmaceutical Preparations

The compounds will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds may also be combined with any other drugs useful in the inhibition of cGMP-PDEs, such as cGMP-PDE5.

The compounds, their pharmaceutically acceptable salts, and pharmaceutically acceptable solvates of either entity can be administered alone but, in human therapy will generally be administered in admixture with a suitable pharmaceutical excipient diluent or carrier selected with regard to the intended route of administration and standard pharmaceutical practice.

For example, the compounds or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, or controlled-release such as sustained-, dual-, or pulsatile delivery applications. The compounds may also be administered via intracavernosal injection. The compounds may also be administered via fast dispersing or fast dissolving dosages forms.

Such tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropyimethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds can also be administered parenterally, for example, intracavernosally, intravenously, intra-arterially, intraperitoneally, intrathecally, intraventricularly, intraurethrally intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds or salts or solvates thereof will usually be from 10 to 500 mg (in single or divided doses).

Thus, for example, tablets or capsules of the compounds or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), compounds may be taken as a single dose on an "as required" basis (i.e. as needed or desired).

Example Tablet Formulation

In general a tablet formulation could typically contain between about 0.01 mg and 500 mg of the compound (or a salt thereof) whilst tablet fill weights may range from 50 mg to 1000 mg. An example formulation for a 10 mg tablet is illustrated:

| Ingredient | % w/w |
|---|---|
| "Active" Compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

Such tablets can be manufactured by standard processes, for example, direct compression or a wet or dry granulation process. The tablet cores may be coated with appropriate overcoats.

The compounds can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Aerosol or dry powder formulations are preferably arranged so that each metered dose or "puff" contains from 1 to 50 mg of the compound for delivery to the patient. The overall daily dose with an aerosol will be in the range of from 1 to 50 mg which may be administered in a single dose or, more usually, in divided doses throughout the day.

The compounds may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds or salts or solvates thereof can be administered in the form of a suppository or pessary, or they may be applied topically in the form of a gel, hydrogel, lotion, solution, cream, ointment or dusting powder. The compounds or salts or solvates thereof may also be dermally administered. The compounds or salts or solvates thereof may also be transdermally administered, for example, by the use of a skin patch. They may also be administered by the ocular, pulmonary or rectal routes.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration of the compounds is the preferred route, being the most convenient and, for example in MED, avoiding the well-known disadvantages associated with intracavernosal (i.c.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, the compound, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus, according to a further aspect there is provided a pharmaceutical formulation including a compound as detailed hereinbefore in admixture with a pharmaceutically or veterinarily acceptable adjuvant, diluent or carrier.

In addition to the fact that the compounds inhibit cyclic guanosine 3',5'-monophosphate phosphodiesterases (cGMP PDEs) and in particular, are potent and selective inhibitors of cGMP PDE5, the compounds may also have the advantage that they may be more efficacious than, be less toxic than, have a broader range of activity than, be more potent than, produce fewer side effects than, be more easily absorbed than, or they may have other useful pharmacological properties over, compounds known in the prior art.

Bioavailability

Preferably the compounds of the invention are orally bioavailable. Oral bioavailablity refers to the proportion of an orally administered drug that reaches the systemic circulation. The factors that determine oral bioavailability of a drug are dissolution, membrane permeability and metabolic stability. Typically, a screening cascade of firstly in vitro and then in vivo techniques is used to determine oral bioavailablity.

Dissolution, the solubilisation of the drug by the aqueous contents of the gastro-intestinal tract (GIT), can be predicted from in vitro solubility experiments conducted at appropriate pH to mimic the GIT. Preferably the compounds of the invention have a minimum solubility of 50 mcg/ml. Solubility can be determined by standard procedures known in the art such as described in Adv. Drug Deliv. Rev. 23, 3–25, 1997.

Membrane permeability refers to the passage of the compound through the cells of the GIT. Lipophilicity is a key property in predicting this and is defined by in vitro Log $D_{7.4}$ measurements using organic solvents and buffer. Preferably the compounds of the invention have a Log $D_{7.4}$ of −2 to +4, more preferably −1 to +2. The log D can be determined by standard procedures known in the art such as described in J. Pharm. Pharmacol. 1990, 42:144.

Cell monolayer assays such as $CaCo_2$ add substantially to prediction of favourable membrane permeability in the presence of efflux transporters such as p-glycoprotein, so-called caco-2 flux. Preferably, compounds of the invention have a caco-2 flux of greater than $2\times10^{-6}$ $cms^{-1}$, more preferably greater than $5\times10^{-6}$ $cms^{-1}$. The caco flux value can be determined by standard procedures known in the art such as described in J. Pharm. Sci, 1990, 79, 595–600.

Metabolic stability addresses the ability of the GIT or the liver to metabolise compounds during the absorption process: the first pass effect. Assay systems such as microsomes, hepatocytes etc are predictive of metabolic liability. Preferably the compounds of the Examples show metabolic stablity in the assay system that is commensurate with an hepatic extraction of less then 0.5. Examples of assay systems and data manipulation are described in Curr. Opin. Drug Disc. Devel., 201, 4, 36–44, Drug Met. Disp.,2000, 28, 1518–1523.

Because of the interplay of the above processes further support that a drug will be orally bioavailable in humans can be gained by in vivo experiments in animals. Absolute bioavailability is determined in these studies by administering the compound separately or in mixtures by the oral route. For absolute determinations (% absorbed) the intravenous route is also employed. Examples of the assessment of oral bioavailability in animals can be found in Drug Met. Disp., 2001, 29, 82–87; J. Med Chem, 1997, 40, 827–829, Drug Met. Disp., 1999, 27, 221–226.

The biological activities of the compounds were determined by the following test methods.

Phosphodiesterase (PDE) Inhibitory Activity

The compounds of the present invention are potent and selective cGMP PDE5 inhibitors. In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human platelets, human cardiac ventricle, human skeletal muscle and human and canine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue or human platelets; the cGMP-stimulated PDE (PDE2) was obtained from human corpus cavernosum or human platelets; the calcium/calmodulin (Ca/CAM)-dependent PDE (PDE1) from human cardiac ventricle; the cAMP-specific PDE (PDE4) from recombinant clone or human skeletal muscle; and the photoreceptor PDE (PDE6) from canine or human retina. Phosphodiesterases 7–11 were generated from full length human recombinant clones transfected into SF9 cells.

Assays were performed either using a modification of the "batch" method of W. J. Thompson et al. (Biochem., 1979, 18, 5228) or using a scintillation proximity assay for the direct detection of AMP/GMP using a modification of the protocol described by Amersham plc under product code TRKQ7090/7100. In summary, the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a conc ~1/2 $K_m$) such that $IC_{50} \cong K_i$. The final assay volume was made up to 102 μl with assay buffer [20 mM Tris-HCl pH 7.4, 5 mM $MgCl_2$, 1 mg/ml bovine serum albumin]. Reactions were initiated with enzyme, incubated for 30–60 min at 30° C. to give <30% substrate turnover and terminated with 50 μl yttrium silicate SPA beads (containing 3 mM of the respective unlabelled cyclic nucleotide for PDEs 3, 9 and 11). Plates were re-sealed and shaken for 20 min, after which the beads were allowed to settle for 30 min in the dark and then counted on a TopCount plate reader (Packard, Meriden, Conn.). Radioactivity units were converted to % activity of an uninhibited control (100%), plotted against inhibitor concentration and inhibitor $IC_{50}$ values obtained using the 'Fit Curve' Microsoft Excel extension or in-house equivalent. Results from these tests show that the compounds of the present invention are potent and selective inhibitors of cGMP-specific PDE5.

Preferred compounds of formula (I) herein have $IC_{50}$ values of less than or equal to about 30 nM for the PDE5 enzyme. A more preferred group of compounds have $IC_{50}$ values of less than or equal to about 10 nM for the PDE5 enzyme. An additional group of compounds having $IC_{50}$ values of less than about 5 nM for the PDE5 enzyme are further preferred.

Especially preferred herein are compounds which have an $IC_{50}$ value of less than about 10, more preferably less than about 5 nM for the PDE5 enzyme in combination with greater than 10-fold selectivity for the PDE5 enzyme versus the PDE6 enzyme. Highly preferred are compounds having $IC_{50}$ values of less than about 10, more preferably less than about 5 nM for the PDE5 enzyme in combination with greater than 20-fold, preferably greater than 30-fold and especially greater than 40-fold selectivity for the PDE5 enzyme versus the PDE6 enzyme.

Functional Activity

This was assessed in vitro by determining the capacity of a compound of the invention to enhance sodium nitroprusside-induced relaxation of pre-contracted rabbit corpus cavernosum tissue strips, as described by S. A. Ballard et al. (Brit. J. Pharmacol., 1996, 118 (suppl.), abstract 153P).

In vivo Activity

In vivo activity is tested by screening test compounds in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).

Safety Profile

The compounds may be tested at varying i.v and p.o. doses in animals such as mouse and dog, observing for any untoward effects.

Biological Activity

Table 1 illustrates the in vitro cGMP PDE5 inhibitory activities for a range of compounds of the invention.

TABLE 1

| Example | PDE5 $IC_{50}$ (nM) | PDE6 $IC_{50}$ (nM) |
| --- | --- | --- |
| 13 | 11.9 | 609 |
| 2 | 13.8 | 592 |
| 3 | 23.0 | 922 |
| 12 | 1.8 | 163 |
| 6 | 2.2 | 85 |
| 10 | 3.2 | 152 |

EXAMPLES AND PREPARATIONS

The synthesis of the compounds of general formula (I) and of the intermediates for use therein can be achieved by analogy with the processes of the Examples and Preparations hereinafter.

$^1$H nuclear magnetic resonance (NMR) spectra were recorded using either a Varian Unity 300 or a Varian inova 400 spectrometer and were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad.

Mass spectra (m/z) were recorded using a Fisons Instruments Trio mass spectrometer in the thermospray ionisation mode (TSP) or using a Finnigan navigator in electrospray ionisation mode (ES)—positive and/or negative ionisation mode.

As used herein, the term "column chromatography" refers to normal phase chromatography using silica gel (0.04–0.06 mm).

Room temperature includes 20 to 25° C.

Example 1

5-(5-Acetyl-2-butoxyphenyl)-2-(1–Cyclobutyl-3-azetidinyl)-3-ethyl-2,6-dihydro-7H-pyrazolo[4,3-d]pyrimidin-7-one

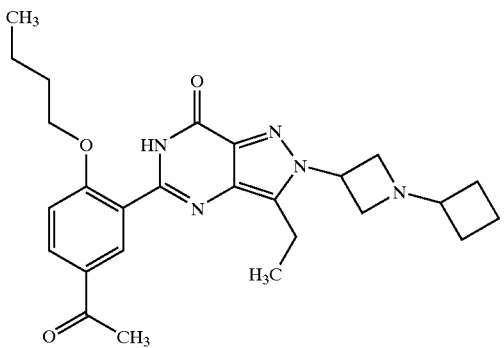

A solution of the azetidine from preparation 14 (500 mg, 0.785 mmol) and cyclobutanone (176 μl, 2.36 mmol) in dichloromethane (4 ml) was stirred at room temperature for 10 minutes, them sodium triacetoxyborohydride (419 mg, 1.86 mmol) added, and the reaction mixture stirred at room temperature for 3 hours. The mixture was diluted with dichloromethane (25 ml) and washed with water and sodium bicarbonate solution. The combined aqueous solutions were extracted with dichloromethane (2×25 ml), and the combined organic solutions then washed with brine, dried (MgSO$_4$) and concentrated under reduced pressure. The crude product was purified by column chromatography on silica gel using dichloromethane:methanol (97.5:2.5) as eluant to give an oil. This was crystallised from diethyl ether, to afford the title compound as a white solid, 210 mg.

$^1$H NMR (CDCl$_3$, 400 MHz) δ: 1.00 (t, 3H), 1.38 (t, 3H), 1.57 (m, 2H), 1.66–1.99 (m, 6H), 2.04 (m, 2H), 2.62 (s, 3H), 3.02 (q, 2H), 3.34 (m, 1H), 3.80 (d, 4H), 4.25 (t, 2H), 5.16 (m, 1H), 7.11 (d, 1H), 8.06 (dd, 1H), 8.95 (d, 1H), 10.54 (s, 1H).

LRMS: m/z (TSP$^+$) 464.2 [MH$^+$]

Microanalysis found: C, 66.88; H, 7.30; N, 14.85. C$_{26}$H$_{33}$N$_5$O$_3$; 0.05H$_2$O requires C, 67.23; H, 7.18; N, 15.08%.

Examples 2 to 4

The following compounds of general formula:

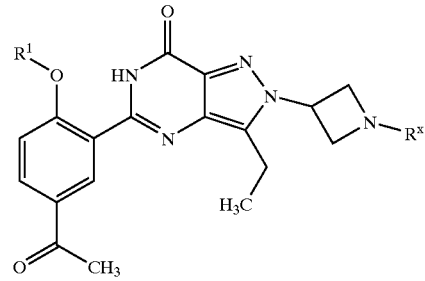

were prepared from the appropriate azetidine compounds (preparations 14 and 15) and ketones, following similar procedures to that described in example 1.

| Ex | R³ | Rˣ | Yield (%) | Data |
|---|---|---|---|---|
| 2 | CH(CH₃)CH₂— with CH₃ | cyclobutyl | 50 white solid | $^1$H NMR(CDCl$_3$, 400 MHz) δ: 1.08(d, 6H), 1.36(t, 3H), 1.63–1.92(m, 4H), 2.01(m, 2H), 2.26(m, 1H), 2.60(s, 3H), 3.00(q, 2H), 3.30(m, 1H), 3.79(d, 4H), 4.00(d, 2H), 5.15(m, 1H), 7.05(d, 1H), 8.02(d, 1H), 8.88(s, 1H), 10.48(s, 1H). LRMS: m/z(TSP$^+$) 464.2[MH$^+$] Microanalysis found: C, 66.24; H, 7.34; N, 14.43. C$_{26}$H$_{33}$N$_5$O$_3$; 0.5H$_2$O requires C, 66.08; H, 7.25; N, 14.82%. |
| 3[1] | n-butyl | CH(CH₃)₂ | 18 white solid | $^1$H NMR(CDCl$_3$, 400 MHz) δ: 1.01(m, 9H), 1.39(t, 3H), 1.58(m, 2H), 1.98(m, 2H), 2.62(m, 4H), 3.02(q, 2H), 3.78(dd, 2H), 3.92(dd, 2H), 4.28(t, 2H), 5.15(m, 1H), 7.10(d, 1H), 8.08(dd, 1H), 8.98(d, 1H), 10.55(s, 1H). LRMS: m/z(TSP$^+$) 452.2[MH$^+$] Microanalysis found: C, 65.97; H, 7.37; N, 15.36. C$_{25}$H$_{33}$N$_5$O$_3$; 0.25H$_2$O requires C, 65.84; H, 7.40; N, 15.36%. |
| 4[1] | CH(CH₃)CH₂— with CH₃ | CH(CH₃)₂ | 38 white solid | $^1$H NMR(CDCl$_3$, 400 MHz) δ: 1.00(d, 6H), 1.10(d, 6H), 1.38(t, 3H), 2.30(m, 1H), 2.61(m, 4H), 3.01(q, 2H), 3.78(dd, 2H), 3.90(dd, 2H), 4.02(d, 2H), 5.15(m, 1H), 7.09(d, 1H), 8.05(dd, 1H), 8.94(d, 1H), 10.50(s, 1H). LRMS: m/z 452.1[MH$^+$] Microanalysis found: C, 65.32; H, 7.36; N, 14.92. C$_{26}$H$_{33}$N$_5$O$_3$; 0.5H$_2$O requires C, 66.08; H, 7.25; N, 14.82%. |

[1] = 2 eq of triethylamine were also used in the reaction

Example 5 tert-Butyl-5-[(5-acetyl-2-propoxyphenyl)-3-ethyl-7-oxo-6,7-dihydro-1H-pyrazolo[4,3-d]pyrimidin-1-yl]-acetate and

Example 6 tert-Butyl-5-r(5-acetyl-2-propoxyphenyl)-3-ethyl-7-oxo-6,7-dihydro-2H-pyrazolo[4,3-d]pyrimidin-2-yl]-acetate

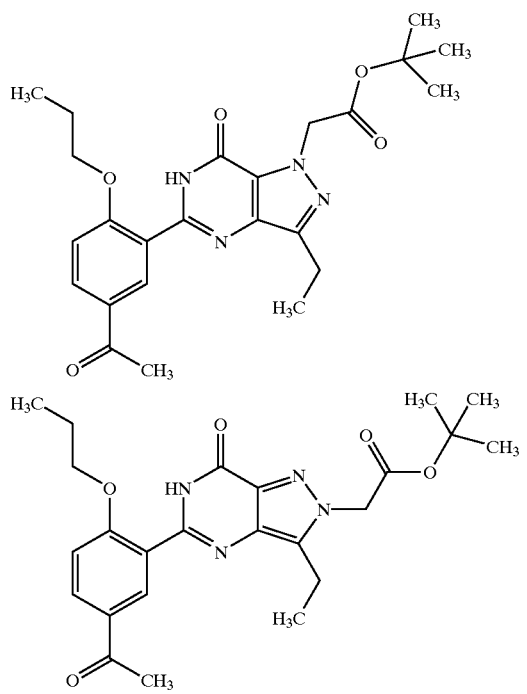

tert-Butyl bromoacetate (295 µl, 2 mmol) was added to a suspension of cesium carbonate (652 mg, 2 mmol) and the pyrazole from preparation 17 (680 mg, 2 mmol) in N,N-dimethylformamide (15 ml) at room temperature, and the reaction was stirred for 18 hours. The mixture was quenched with water and extracted with diethyl ether (5×30 ml) and ethyl acetate (3×20 ml). The diethyl ether extracts were dried over $Na_2SO_4$, concentrated under reduced pressure and purified by column chromatography on silica gel using dichloromethane:methanol:0.88 ammonia (95:5:0.5) and the product was recrystallised from dichloromethane/diisopropylether to afford the title compound of example 5 as a white solid, 171 mg.

$^1$H NMR (CDCl$_3$, 400 MHz) δ: 1.19 (t, 3H), 1.47 (m, 12H), 2.03 (m, 2H), 2.68 (s, 3H), 3.06 (q, 2H), 4.26 (t, 2H), 5.24 (s, 2H), 7.14 (d, 1H), 8.13 (d, 1H), 9.07 (s, 1H), 10.92 (br s, 1H).

LRMS: m/z (TSP$^+$) 455.7 [MH$^+$].

Microanalysis found: C, 63.29; H, 6.66; N, 12.24. $C_{24}H_{30}N_4O_5$ requires C, 63.42; H, 6.65; N, 12.33%.

The ethyl acetate extracts were dried over $Na_2SO_4$, concentrated under reduced pressure and purified by column chromatography on silica gel using dichloromethane:methanol:0.88 ammonia (95:5:0.5) as eluant and the product was recrystallised from dichloromethane/diisopropylether to afford the title compound of example 6 as a white solid, 112 mg.

$^1$H NMR (CDCl$_3$, 400 MHz) δ: 1.17 (t, 3H), 1.46 (m, 12H), 2.02 (m, 2H), 2.66 (s, 3H), 3.01 (q, 2H), 4.24 (t, 2H), 5.03 (s, 2H), 7.14 (d, 1H), 8.09 (d, 1H), 8.99 (s, 1H), 10.60 (br s, 1H).

LRMS: m/z (TSP$^+$) 455.4 [MH$^+$].

Microanalysis found: C, 62.96; H, 6.65; N, 12.21. $C_{24}H_{30}N_4O_5$ requires C, 63.42; 15H, 6.65; N, 12.33%.

Example 7 tert-Butyl-3-[(5-acetyl-2-propoxyphenyl)-3-ethyl-7-oxo-6,7-dihydro-1H-pyrazolo[4,3-d]pyrimidin-1-yl]-2-methylpropanoate

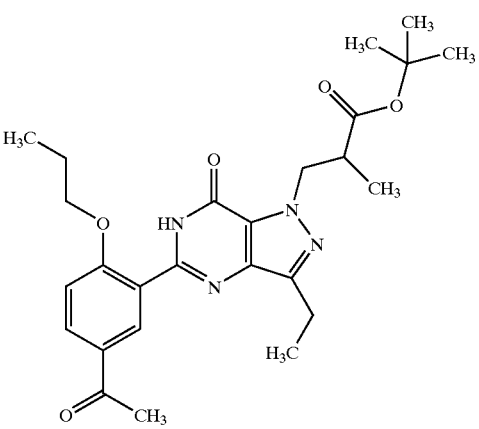

2-Bromo-tert-butylisobutyrate (446 mg, 2 mmol) was added to a suspension of cesium carbonate (652 mg, 2 mmol) and the pyrazole from preparation 17 (680 mg, 2 mmol) in N,N-dimethylformamide (15 ml) at room temperature, and the reaction was stirred for 18 hours. Starting material remained by TLC analysis, so the reaction was heated to 60° C. for 36 hours, cooled to room temperature and quenched with water (50 ml). The mixture was extracted with diethyl ether (3×50 ml) and the combined organic extracts were dried over $Na_2SO_4$, concentrated under reduced pressure and purified by column chromatography on silica gel using dichloromethane:methanol:0.88 ammonia (95:5:0.5) as eluant and the product was recrystallised from diisopropylether to afford the title compound as a white solid, 55 mg.

$^1$H NMR (CDCl$_3$, 300 MHz) δ: 1.17 (m, 6H), 1.44 (m, 12H), 2.02 (m, 2H), 2.66 (s, 3H), 3.12 (q, 2H), 3.38 (m, 1H), 4.22 (m, 3H), 4.60 (dd, 1H), 7.13 (d, 1H), 8.08 (d, 1H), 9.00 (s, 1H), 10.60 (br s, 1H).

LRMS: m/z (TSP$^+$) 483.3 [MH$^+$].

Microanalysis found: C, 64.44; H, 7.09; N, 11.63. $C_{26}H_{34}N_4O_5$ requires C, 64.70; H, 7.10; N, 11.61%.

Example 8

Ethyl 2-[5-(5-acetyl-2-propoxyphenyl)-3-ethyl-7-oxo-6,7-dihydro-2H-pyrazolo[4,3-d]pyrimidin-2-yl]propanoate

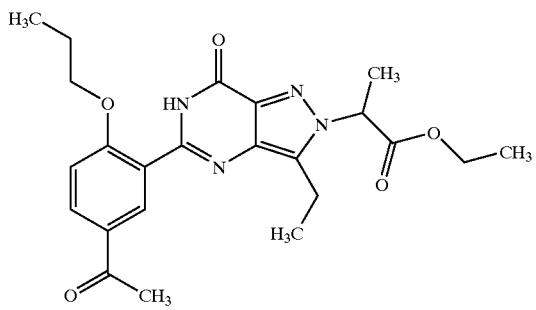

Ethyl-2-bromopropanoate (362 mg, 2 mmol) was added to a suspension of cesium carbonate (652 mg, 2 mmol) and the pyrazole from preparation 17 (680 mg, 2 mmol) in N,N-dimethylformamide (15 ml) at room temperature, and the reaction was stirred at 60° C. for 13 hours, cooled to room temperature and quenched with water (50 ml). The mixture was extracted with diethyl ether (3×50 ml) and ethyl acetate (3×50 ml) and the combined organic extracts were dried over $Na_2SO_4$, concentrated under reduced pressure and purified by column chromatography on silica gel using dichloromethane:methanol:0.88 ammonia (97.5:2.5:0.25) as eluant. This gave two products, the most polar of which was crystallised from diisopropylether to afford the title compound as a white solid, 98 mg.

$^1$H NMR (CDCl$_3$, 300 MHz) δ: 1.13 (t, 3H), 1.23 (t, 3H), 1.43 (t, 3H), 2.00 (m, 5H), 2.65 (s, 3H), 3.05 (q, 2H), 4.21 (m, 4H), 5.21 (m, 1H), 7.10 (d, 1H), 8.08 (d, 1H), 8.98 (s, 1H), 10.55 (brs, 1H).

LRMS: m/z (ESP$^+$) 441 [MH$^+$], 463 [MNa$^+$].

Microanalysis found: C, 62.53; H, 6.39; N, 12.66. $C_{23}H_{28}N_4O_5$ requires C, 62.71; H, 6.41; N, 12.66%.

Example 9
Methyl-4-[5-(5-acetyl-2-propoxyphenyl)-3-ethyl-7-oxo-6,7-dihydro-1H-pyrazolo[4,3-d]pyrimidin-1-yl]-butanoate and

Example 10
Methyl-4-[5-(5-acetyl-2-propoxyphenyl)-3-ethyl-7-oxo-6,7-dihydro-2H-pyrazolo[4,3-d]pyrimidin-1-yl]-butanoate

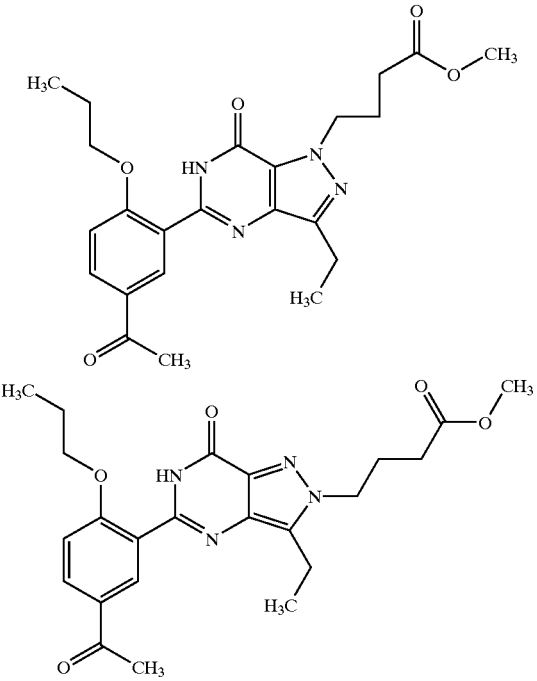

Methyl 4-bromobutanoate (370 mg, 2 mmol) was added to a suspension of cesium carbonate (652 mg, 2 mmol) and the pyrazole from preparation 17 (680 mg, 2 mmol) in N,N-dimethylformamide (15 ml) at room temperature, and the reaction was stirred for 64 hours. The mixture was quenched with water and extracted with diethyl ether (4×20 ml) and ethyl acetate (2×20 ml). The ethyl acetate extracts were washed with water (2×20 ml), brine, dried over $Na_2SO_4$ and concentrated under reduced pressure. The residue was purified by column chromatography on silica gel using dichloromethane:methanol:0.88 ammonia (97.5:2.5:0.25) and the least polar fraction was collected and recrystallised twice from acetonitrile to afford the title compound of example 9 as a white solid, 31 mg.

$^1$H NMR (CDCl$_3$, 400 MHz) δ: 1.19 (t, 3H), 1.43 (t, 3H), 2.04 (m, 2H), 2.28 (m, 2H), 2.39 (m, 2H), 2.66 (s, 3H), 3.01 (q, 2H), 3.65 (s, 3H), 4.27 (t, 2H), 4.66 (t, 2H), 7.15 (d, 1H), 8.14 (d, 1H), 9.08 (s, 1H), 10.91 (brs, 1H).

LRMS: m/z(ESP$^+$)441 [MH$^+$], 439 [MH$^-$].

Microanalysis found: C, 62.21; H, 6.45; N, 12.51. $C_{23}H_{28}N_4O_5$. 0.2 mol $H_2O$ requires C, 62.21; H, 6.45; N, 12.62%.

The other fractions were combined and re-chromatographed eluting with pentane:isopropyl alcohol:0.88 ammonia (80:20:1.5). This gave two major products, the most polar of which was triturated with diisopropylether to afford the title compound of example 10 as a white solid, 12.4 mg.

$^1$H NMR (CDCl$_3$, 300 MHz) δ: 1.16 (t, 3H), 1.45 (t, 3H), 2.01 (m, 2H), 2.34 (m, 2H), 2.42 (m, 2H), 2.66 (s, 3H), 3.06 (q, 2H), 3.70 (s, 3H), 4.24 (t, 2H), 4.40 (t, 2H), 7.13 (d, 1H), 8.10 (d, 1H), 8.99 (s, 1H), 10.59 (brs, 1H).

LRMS: m/z (ESP$^+$) 441 [MH$^+$], 463 [MNa$^+$], 439 [MH$^-$].

Microanalysis found: C, 62.24; H, 6.37; N, 12.57. $C_{23}H_{28}N_4O_5$ requires C, 62.71; H, 6.41; N, 12.72%.

Example 11

4-[5-(5-Acetyl-2-propoxyphenyl)-3-ethyl-7-oxo-6,7-dihydro-1H-pyrazolo[4,3-d]pyrimidin-1-yl]butanoic Acid

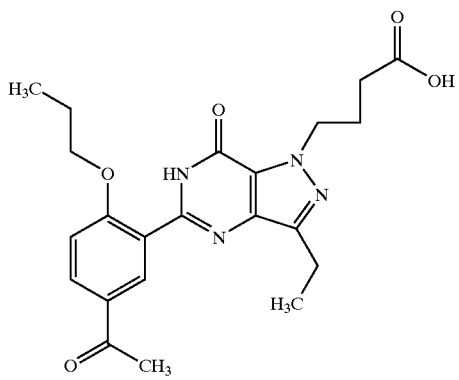

1N Sodium hydroxide solution (1 ml, 1 mmol) was added to a solution of the ester from example 9 (30 mg, 0.07 mmol) in dioxan (1 ml) and the reaction was stirred at room temperature for 2.5 hours. The reaction was adjusted to pH 2 with 2N hydrochloric acid, stirred for 30 min and the resulting precipitate was filtered and washed with water. The product was dried in vacuo to afford the title compound as a white solid, 13 mg.

$^1$H NMR (CDCl$_3$, 400 MHz) δ: 1.18 (t, 3H), 1.43 (t, 3H), 2.04 (m, 2H), 2.30 (m, 2H), 2.41 (m, 2H), 2.68 (s, 3H), 3.02 (q, 2H), 4.27 (t, 2H), 4.72 (t, 2H), 7.13 (d, 1H), 8.12 (d, 1H), 9.02 (s, 1H), 11.06 (brs, 1H).

LRMS: m/z (ESP$^+$) 427 [MH$^+$], 449 [MNa$^+$], 425 [MH$^-$].

Microanalysis found: C, 61.45; H, 6.16; N, 12.92. C$_{22}$H$_{26}$N$_4$O$_5$. 0.2 mol H$_2$O requires C, 61.44; H, 6.19; N, 13.03%.

Example 12

4-[5-(5-Acetyl-2-propoxyphenyl)-3-ethyl-7-oxo-6,7-dihydro-2H-pyrazolo[4,3-d]pyrimidin-2-yl]butanoic Acid

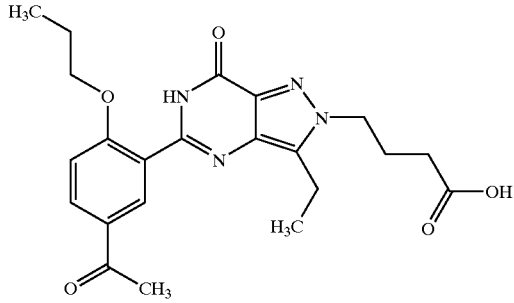

1N Sodium hydroxide solution (1 ml, 1 mmol) was added to a solution of the ester from example 10 (25 mg, 0.06 mmol) in dioxan (1 ml) and the reaction was stirred at room temperature for 3 hours. The reaction was adjusted to pH 2 with 2N hydrochloric acid, diluted with water (5 ml) and half of the solvent was removed under reduced pressure. The resulting precipitate was filtered, washed with water, dried in vacuo and slurried with acetonitrile. The slurry was then filtered and the solid was dried in vacuo to afford the title compound as a white solid, 13 mg.

$^1$H NMR (CDCl$_3$, 300 MHz) δ: 1.15 (t, 3H), 1.45 (t, 3H), 2.01 (m, 2H), 2.35 (m, 2H), 2.49 (m, 2H), 2.67 (s, 3H), 3.09 (q, 2H), 4.26 (t, 2H), 4.42 (t, 2H), 7.13 (d, 1H), 8.11 (d, 1H), 8.95 (s, 1H), 10.73 (br s, 1H).

LRMS: m/z (ESP$^+$) 427 [MH$^+$], 449 [MNa$^+$]

Microanalysis found: C, 61.41; H, 6.12; N, 12.85. C$_{22}$H$_{26}$N$_4$O$_5$. 0.2 mol H$_2$O requires C, 61.44; H, 6.19; N, 13.03%.

Example 13

2-[5-(5-Acetyl-2-propoxyphenyl)-3-ethyl-7-oxo-6,7-dihydro-2H-pyrazolo[4,3-d]pyrimidin-2-yl]-N,N-dimethylacetamide

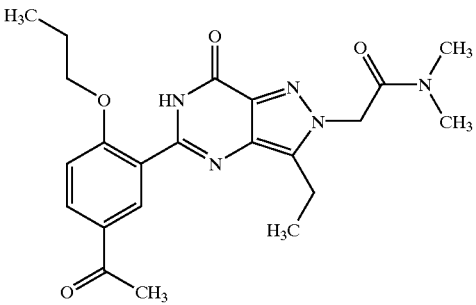

2-Chloro-N,N-dimethylacetamide (178 mg, 1.47 mmol) was added to a suspension of cesium carbonate (480 mg, 1.47 mmol) and the pyrazole from preparation 17 (500 mg, 1.47 mmol) in N,N-dimethylformamide (10 ml) at room temperature, and the reaction was stirred for 84 hours. The mixture was quenched with water and stood at room temperature for 18 hours, and the resultant white solid was isolated by filtration and washed with water, before being dried in vacuo. The solid was purified by column chromatography on silica gel using dichloromethane:methanol:0.88 ammonia (95:5:0.5) to give two products, the most polar of which was collected and crystallised from acetonitrile to afford the title compound as a white solid, 132 mg.

$^1$H NMR (CDCl$_3$, 400 MHz) δ: 1.15 (t, 3H), 1.47 (t, 3H), 2.00 (m, 2H), 2.64 (s, 3H), 3.05 (m, 5H), 3.18 (s, 3H), 4.23 (m, 2H), 5.20 (s, 2H), 7.11 (d, 1H), 8.10 (d, 1H), 8.98 (s, 1H), 11.04 (br s, 1H).

LRMS: m/z (ESP$^+$) 426 [MH$^+$], 448 [MNa$^+$].

Microanalysis found: C, 61.95; H, 6.38; N, 16.55. C$_{22}$H$_{27}$N$_5$O$_4$ requires C, 61.95; H, 6.40; N, 16.46%.

Example 14

5-(5-Acetyl-2-propoxyphenyl)-3-propyl-2-(2-pyridinylmethyl)-2,6-dihydro-7H-pyrazolo[4,3-d]pyrimidin-7-one

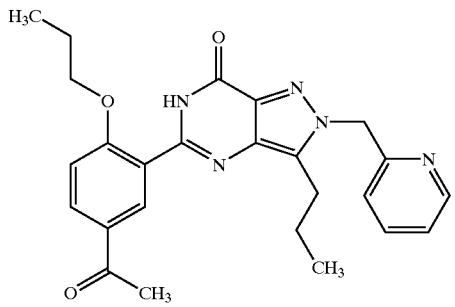

Polyphosphoric acid (20 g) and the pyrazole carboxamide from preparation 18 (1.3 g, 2.8 mmol) were heated to 190–200° C. for 15 min and the reaction was cooled to room temperature. The mixture was quenched with water, basified to pH 8 with sodium carbonate and extracted with dichloromethane (×2). The combined organic extracts were dried over $Na_2SO_4$, concentrated under reduced pressure and the residue was purified by column chromatography on silica gel using dichloromethane:methanol (100:0 changing to 99:1 then 94:6) to afford the title compound as an off-white solid, 30 mg.

$^1$H NMR ($CDCl_3$, 400 MHz) δ: 0.98 (t, 3H), 1.16 (t, 3H), 1.78 (m, 2H), 2.03 (m, 2H), 2.63 (s, 3H), 3.00 (t, 2H), 4.25 (t, 2H), 5.69 (s, 2H), 7.09 (m, 2H), 7.22 (m, 1H), 7.62 (t, 1 H), 8.09 (d, 1H), 8.58 (d, 1H), 8.99 (s, 1H), 10.62 (br s, 1H).
LRMS: m/z ($TSP^+$) 446.2 $[MH^+]$.

Preparation 1
4-(2-n-Propoxybenzamido)-3-n-propyl-1H-pyrazole-5–Carboxamide

A solution of 2-n-propoxybenzoyl chloride (57.6 g, 0.291 mol) in dichloromethane (50 ml) was added dropwise to a stirred, ice-cooled suspension of 4-amino-3-propyl-1H-pyrazole-5–Carboxamide (the compound of Preparation 8 of WO 98/49166) (35.0 g, 0.208 mol) in dry pyridine (350 ml) and the resulting mixture stirred for 18 hours at room temperature, then evaporated under reduced pressure. The residue was azeotroped with toluene (2×100 ml) and the resulting brown solid triturated with ether (100 ml) to give the title compound (83.0 g) as a beige solid.

δ ($CH_3OHd_4$): 0.92 (3H,t), 1.14 (3H,t), 1.65 (2H,m), 1.94 (2H,m), 2.80 (2H,t), 4.20 (2H,t), 7.08 (1H,m), 7.18 (1H,d), 7.52 (1H,m), 8.04 (1H,d). LRMS: m/z 331 $(M+1)^+$.

Preparation 2
5-(2-n-Propoxyphenyl)-3-n-propyl-1,6-dihydro-7H-pyrazolo[4,3-d]pyrimidin-7-one Potassium t-butoxide (93.0 g, 0.832 mol) was added portionwise to a stirred solution of the title compound of Preparation 1 (83.0 g, 0.25 mol) in propan-2-ol (800 ml) under nitrogen and the mixture heated for 18 hours under reflux, then allowed to cool. Water (100 ml) was added, to produce a homogeneous solution which was acidified to pH 6 with 2M hydrochloric acid. The resulting white precipitate was collected and dried by suction to provide the title compound (37.4 g). Found: C, 65.36; H, 6.49; N, 17.99. $C_{17}H_{20}N_4O_2$ requires C, 65.37; H, 6.45; N, 17.94%. δ ($CDCl_3$): 1.05 (3H,t), 1.16 (3H,t), 2.00 (4H,m), 3.04 (2H,t), 4.20 (2H,t), 7.07 (1H,d), 7.16 (1H,m), 7.48 (1H,m), 8.52 (1H,d), 11.30 (1H,s), 12.25 (1H,s). LRMS: m/z 313 $(M+1)^+$.

Preparation 3
2–Cyanomethyl-5-(2-n-propoxyphenyl)-3-n-propyl-2,6-dihydro-7H-pyrazolo[4,3-d]pyrimidin-7-one A 2M solution of sodium bis(trimethylsilyl)amide in tetrahydrofuran (4.42 ml, 8.8 mmol) was added to a stirred, ice-cooled solution of the title compound of Preparation 2 (2.3 g, 7.4 mmol) in tetrahydrofuran (25 ml) and the resulting solution stirred for 30 minutes, before being cooled to about –70° C. Bromoacetonitrile (0.54 ml, 7.7 mmol) was added dropwise, the cooling bath removed and, after a further 20 hours, the reaction mixture carefully quenched with methanol (5 ml) and evaporated under reduced pressure. The residue was purified by column chromatography on silica gel, using an elution gradient of dichloromethane:methanol (99:1 to 95:5), followed by crystallisation from hexane:ethyl acetate, to afford the title compound (1.89 g) as a white solid. Found: C, 64.84; H, 5.98; N, 19.71. $C_{19}H_{21}N_5O_2$ requires C, 64.94; H, 6.02; N, 19.93%. δ ($CDCl_3$): 1.12 (6H,m), 1.98 (4H,m), 3.08 (2H,t), 4.20 (2H,t), 5.26 (2H,s), 7.05 (1H,d), 7.16 (1H,m), 7.48 (1H,m), 8.42 (1H,d), 11.00 (1H,s). LRMS: m/z 703 $(2M+1)^+$.

Haloketones of the structure illustrated may be prepared via Friedel-Crafts chemistry on intermediates such as the title compound of Preparation 3 such as in known in the art.

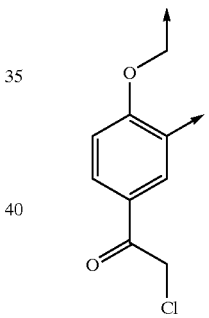

Reaction of this halo ketone with an amine provides compounds having $R^4$ functionality as detailed hereinbefore.

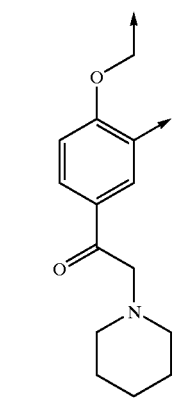

Preparation 4
Methyl 5-acetyl-2-butoxybenzoate

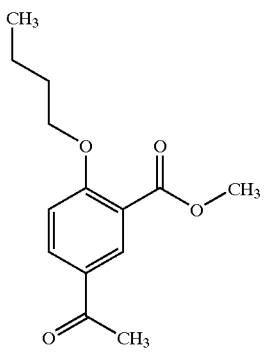

n-Butyl iodide (13.2 ml, 117 mmol) was added to a mixture of methyl 5-acetylsalicylate (15 g, 77 mmol) and potassium carbonate (16 g, 117 mmol) in acetonitrile (500 ml), and the reaction stirred at 60° C. for 18 hours. TLC analysis showed starting material remaining, so additional n-butyl iodide (26.4 ml, 234 mmol) and potassium carbonate (16 g, 117 mmol) were added and the reaction stirred at 60° C. for a further 72 hours. The cooled mixture was concentrated under reduced pressure and the residue partitioned between ethyl acetate and water. The phases were separated, the organic layer washed with brine, dried (MgSO$_4$) and evaporated under reduced pressure to afford the title compound as a yellow oil that crystallised on drying in vacuo, 17.4 g.

$^1$H NMR (CDCl$_3$, 400 MHz) □: 0.99 (t, 3H), 1.54 (m, 2H), 1.82 (m, 2H), 2.58 (s, 3H), 3.90 (s, 3H), 4.11 (t, 2H), 7.00 (d, 1H), 8.06 (dd, 1H), 8.38 (d, 1H).

LRMS: m/z (TSP$^+$) 251.1 [MH$^+$]

Preparation 5
Methyl 5-acetyl-2-isobutoxybenzoate

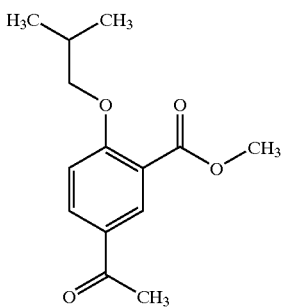

1-Iodo-2-methylpropane (13.35 ml, 117 mmol) was added to a mixture of methyl 5-acetylsalicylate (15 g, 77 mmol) and potassium carbonate (16 g, 117 mmol) in acetonitrile (500 ml), and the reaction stirred at 60° C. for 18 hours. TLC analysis showed starting material remaining, so additional 1-iodo-2-methylpropane (26.7 ml, 234 mmol) and potassium carbonate (16 g, 117 mmol) were added and the reaction stirred at 60° C. for a further 72 hours. TLC analysis showed starting material still remaining, so additional 1-iodo-2-methylpropane (13.35 ml, 117 mmol) and potassium carbonate (16 g, 117 mmol) were added and the reaction stirred at reflux for a further 3 hours. The cooled mixture was concentrated under reduced pressure and the residue partitioned between ethyl acetate and 1N sodium hydroxide solution. The phases were separated, the aqueous extracted with further ethyl acetate, and the combined organic solutions washed with brine, dried (MgSO$_4$) and evaporated under reduced pressure to give the title compound as a brown oil, 8.3 g.

$^1$H NMR (CDCl$_3$, 400 MHz) δ: 1.05 (d, 6H), 2.16 (m, 1H), 2.58 (s, 3H), 3.85 (d, 2H), 3.90 (s, 3H), 6.99 (d, 1H), 8.08 (dd, 1H), 8.39 (d, 1H).

LRMS: m/z (TSP$^+$) 251.2 [MH$^+$]

Preparation 6
5-Acetyl-2-butoxybenzoic Acid

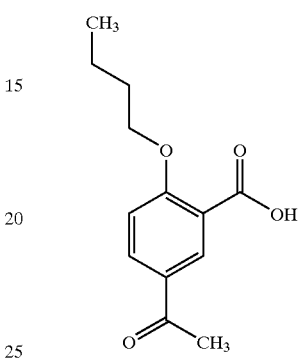

Sodium hydroxide pellets (5.6 g, 139 mmol) were added to a solution of the ester from preparation 4 (17.4 g, 70 mmol) in dioxan (400 ml) and water (40 ml), and the reaction stirred at room temperature for 18 hours. The mixture was concentrated under reduced pressure, the residue acidifed to pH 1 using 2N hydrochloric acid, and the aqueous extracted with dichloromethane (250 ml, 3×100 ml). The combined organic solutions were washed with brine, dried (MgSO$_4$) and evaporated under reduced pressure to give the title compound as an orange solid, 15.16 g.

$^1$H NMR (CDCl$_3$, 400 MHz) □: 1.02 (t, 3H), 1.57 (m, 2H), 1.96 (m, 2H), 2.60 (s, 3H), 4.35 (t, 2H), 7.12 (d, 1H), 8.20 (d, 1H), 8.74 (s, 1H).

LRMS: m/z (TSP$^+$) 237.1 [MH$^+$]

Preparation 7
5-Acetyl-2-isobutoxybenzoic Acid

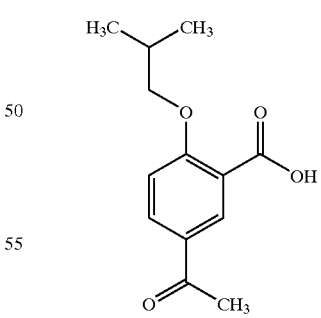

The title compound was obtained in 83% yield from the ester from preparation 5, following the procedure described in preparation 6.

$^1$H NMR (CDCl$_3$, 400 MHz) □: 1.14 (d, 6H), 2.25 (m, 1H), 2.61 (s, 3H), 4.10 (d, 2H), 7.13 (d, 1H), 8.20 (d, 1H), 8.77 (s, 1H).

LRMS: m/z (TSP$^+$) 254.2 [MNH$_4^+$]

Preparation 8
4-[(5-Acetyl-2-butoxybenzoyl)amino]-5-ethyl-1H-pyrazole-3–Carboxamide

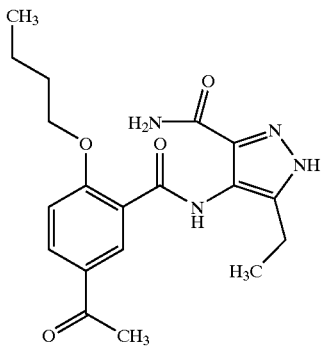

Oxalyl chloride (16.8 ml, 193 mmol) was added to an ice-cooled solution of the acid from preparation 6 (15.16 g, 64 mmol) in N,N-dimethylformamide (0.5 ml) and dichloromethane (300 ml). Once addition was complete, the solution was allowed to warm to room temperature, and stirred for 1.5 hours. The solution was concentrated under reduced pressure and azeotroped with dichloromethane (2×), then dried in vacuo. This intermediate acid chloride was dissolved in dichloromethane (100 ml), triethylamine (27 ml, 193 mmol) added, followed by a solution of 4-amino-3-ethyl-1H-pyrazole-5–Carboxamide (WO 9849166) (9.9 g, 64 mmol) in dichloromethane (200 ml), and the reaction stirred at room temperature for 3 hours. The mixture was washed with sodium bicarbonate solution, this aqueous solution re-extracted with dichloromethane (4×100 ml), and the combined organic extracts dried (MgSO$_4$) and evaporated under reduced pressure. The residual brown solid was triturated with ethyl acetate, the solid filtered, washed with diethyl ether and dried. This solid was further purified by column chromatography on silica gel using dichloromethane:methanol:0.88 ammonia (95:5:0.5) to afford the title compound as a beige solid, 20.12 g.

$^1$H NMR (CDCl$_3$, 400 MHz) □: 0.98 (t, 3H), 1.28 (t, 3H), 1.50 (m, 2H), 1.98 (m, 2H), 2.60 (s, 3H), 2.97 (q, 2H), 4.35 (t, 2H), 5.38 (br s, 1H), 6.78 (br s, 1H), 7.08 (d, 1H), 8.15 (dd, 1H), 8.81 (d, 1H), 10.38 (br s, 1H).

LRMS: m/z (TSP$^+$) 373.0 [MH$^+$]

Microanalysis found: C, 60.85; H, 6.58; N, 14.73. C$_{19}$H$_{24}$N$_4$O$_4$ requires C, 61.28; H, 6.50; N, 15.04%.

Preparation 9
4-[(5-Acetyl-2-isobutoxybenzoyl)amino]-5-ethyl-1H-pyrazole-3-carboxamide

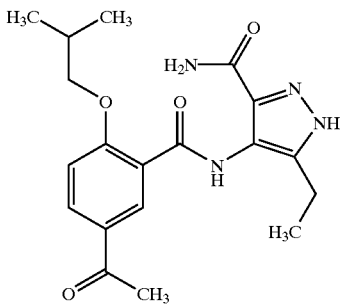

The title compound was obtained as a beige solid in 86% yield from the acid from preparation 7 and 4-amino-3-ethyl-1H-pyrazole-5–Carboxamide (WO 9849166), following a similar procedure to that described in preparation 8.

$^1$H NMR (CDCl$_3$, 400 MHz)]: 1.02 (d, 6H), 1.25 (t, 3H), 2.38 (m, 1H), 2.60 (s, 3H), 2.96 (q, 2H), 4.06 (d, 2H), 5.33 (br s, 1H), 6.78 (br s, 1H), 7.08 (d, 1H), 8.15 (d, 1H), 8.80 (s, 1H), 10.22 (s, 1H).

LRMS: m/z (ES+) 395 [MNa$^+$]

Preparation 10
tert-Butyl 3-[4-[(5-acetyl-2-butoxybenzoyl)amino]-3-(aminocarbonyl)-5-ethyl-1H-pyrazol-1-yl]-1-azetidinecarboxylate

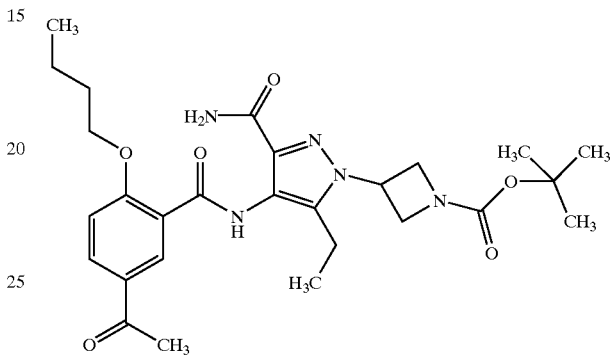

Cesium carbonate (19.7 g, 60.0 mmol) was added to a mixture of the pyrazole carboxamide from preparation 8 (15 g, 40 mmol) and tert-butyl-3-iodo-1-azetidinecarboxylate (EP 992493) (17.4 g, 60.0 mmol) in N,N-dimethylformamide (200 ml) and the reaction stirred at 50° C. for 16 hours. TLC analysis showed starting material remaining, so additional tert-butyl-3-iodo-1-azetidinecarboxylate (EP 992493) (6.0 g, 18.4 mmol) was added and the reaction stirred for a further 18 hours. The mixture was concentrated under reduced pressure and the residue partitioned between ethyl acetate and sodium bicarbonate solution. The resulting solid was filtered off, washed with ether and dried to give the title compound as a white solid, 6.8 g.

The filtrate was separated, the organic layer washed with brine, dried (MgSO$_4$) and evaporated under reduced pressure to give a brown solid. This was triturated with ethyl acetate and warm diethyl ether, filtered and dried in vacuo, to afford additional product as a white solid, 8.2 g, (15.0 g in total).

$^1$H NMR (DMSOd$_6$, 400 MHz) l: 0.88 (t, 3H), 1.06 (t, 3H), 1.40 (m, 11H), 1.82 (m, 2H), 2.54 (s, 3H), 2.70 (m, 2H), 4.26 (m, 6H), 5.32 (m, 1H), 7.32 (m, 2H), 7.50 (br s, 1H), 8.08 (d, 1H), 8.42 (s, 1H), 10.00 (s, 1H).

LRMS: m/z (TSP$^+$) 528.1 [MH$^+$]

Preparation 11
tert-Butyl 3-[4-[(5-acetyl-2-isobutoxybenzoyl)amino]-3-(aminocarbonyl)-5-ethyl-1H-pyrazol-1-yl]-1-azetidinecarboxylate

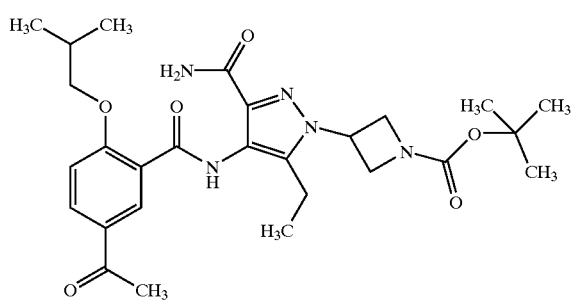

Cesium carbonate (11.4 g, 35 mmol) was added to a mixture of the pyrazole from preparation 9 (8.7 g, 23 mmol) and tert-butyl-3-iodo-1-azetidinecarboxylate (EP 992493) (19.9 g, 35 mmol) in N,N-dimethylformamide (100 ml) and the reaction stirred at 50° C. for 16 hours. The cooled mixture was concentrated under reduced pressure and the residue partitioned between water (250 ml)/saturated sodium bicarbonate solution (200 ml) and ethyl acetate (100 ml). The layers were separated, and the aqueous solution extracted with ethyl acetate (4×100 ml). The combined organic layers were washed with brine, dried (MgSO₄) and evaporated under reduced pressure to give a brown solid. This was purified by column chromatography on silica gel using an elution gradient of dichloromethane:methanol:0.88 ammonia (100:0:0 to 97.5:2.5:0.25) to afford the title compound as a white solid, after trituration from ethyl acetate, 6.33 g.

¹H NMR (CDCl₃, 400 MHz) □: 1.02 (d, 6H), 1.18 (t, 3H), 1.46 (s, 9H), 2.38 (m, 1H), 2.60 (s, 3H), 2.85 (q, 2H), 4.05 (d, 2H), 4.37 (m, 2H), 4.44 (m, 2H), 5.08 (m, 1H), 5.28 (br s, 1H), 6.74 (br s, 1H), 7.06 (d, 1H), 8.14 (dd, 1H), 8.78 (d, 1H), 10.17 (s, 1H).

LRMS: m/z (TSP⁺) 528.2 [MH⁺]

Preparation 12 tert-Butyl 3-[5-(5-acetyl-2-butoxyphenyl)-3-ethyl-7-oxo-6,7-dihydro-2H-pyrazolo[4,3-d]pyrimidin-2-yl]-1-azetidinecarboxylate

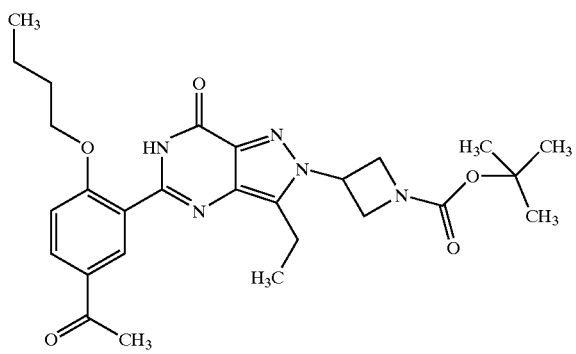

Cesium carbonate (26.8 g, 83 mmol) was added to a mixture of the compound from preparation 10 (14.5 g, 28 mmol), molecular sieves, and n-butyl acetate (3.6 ml, 28 mmol) in n-butanol (150 ml) and the reaction stirred at 140° C. for 10 hours. The cooled mixture was concentrated under reduced pressure, the brown residue partitioned between ethyl acetate and sodium bicarbonate solution, (some sonication required), then filtered. The filtrate was separated, the aqueous layer further extracted with ethyl acetate (4x), and the combined organic solutions washed with brine, dried (MgSO₄) and evaporated under reduced pressure, to give the title compound, 8.3 g.

¹H NMR (CDCl₃, 400 MHz) □: 1.02 (t, 3H), 1.38 (t, 3H), 1.46 (s, 9H), 1.58 (m, 2H), 1.98 (m, 2H), 2.62 (s, 3H), 3.03 (q, 2H), 4.30 (m, 2H), 4.39 (m, 2H), 4.65 (bm, 2H), 5.23 (m, 1H), 7.11 (d, 1H), 8.06 (dd, 1H), 8.98 (d, 1H), 10.60 (s, 1H).

Preparation 13 tert-Butyl 3-[5-(5-acetyl-2-iso-butoxyphenyl)-3-ethyl-7-oxo-6,7-dihydro-2H-pyrazolo[4,3-d]pyrimidin-2-yl]-1-azetidinecarboxylate

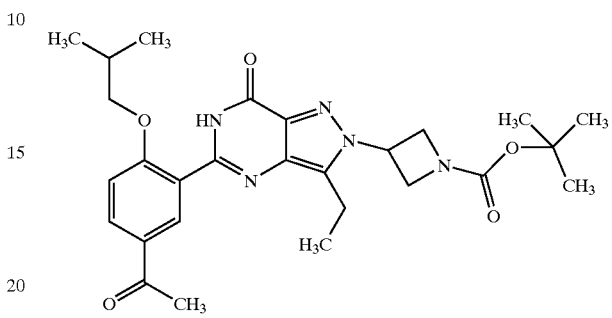

The title compound was obtained in 90% yield as an orange foam, from the compound from preparation 11, iso-butanol and iso-butyl acetate, following a similar procedure to that described in preparation 12.

¹H NMR (CDCl₃, 400 MHz) □: 1.08 (d, 6H), 1.37 (t, 3H), 1.42 (s, 9H), 2.25 (m, 1H), 2.60 (s, 3H), 3.00 (q, 2H), 4.00 (d, 2H), 4.37 (m, 2H), 4.63 (bm, 2H), 5.22 (m, 1H), 7.05 (d, 1H), 8.03 (dd, 1H), 8.90 (d, 1H), 10.52 (s, 1H).

LRMS m/z (TSP⁺) 410.1 [M-Boc]⁺

Preparation 14

5-(5-Acetyl-2-butoxyphenyl)-2-(3-azetidinyl)-3-ethyl-2,6-dihydro-7H-pyrazolo[4,3-d]pyrimidin-7-one trifluoroacetate

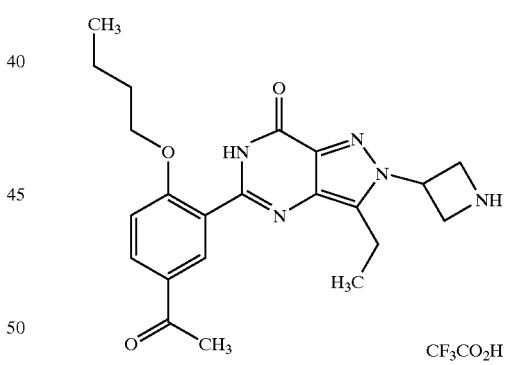

Trifluoroacetic acid (4.3 ml) was added to a solution of the protected azetidine from preparation 12 (2.84 g, 5.58 mmol) in dichloromethane (15 ml), and the reaction stirred at room temperature for 1.5 hours. The solution was evaporated under reduced pressure, and the residual brown gum triturated from dichloromethane (20 ml) and diethyl ether (150 ml). The resulting solid was filtered, washed with further diethyl ether and dried in vacuo, to afford the title compound as a beige solid, 3.06 g.

¹H NMR (CD₃OD, 400 MHz) □: 0.97 (t, 3H), 1.32 (t, 3H), 1.50 (m, 2H), 1.82 (m, 2H), 2.60 (s, 3H), 3.03 (q, 2H), 4.22 (t, 2H), 4.65 (m, 4H), 5.72 (m, 1H), 7.25 (d, 1H), 8.18 (d, 1H), 8.41 (s, 1H).

LRMS:m/z (TSP⁺) 410.1 [MH⁺]

Preparation 15
5-(5-Acetyl-2-isobutoxyphenyl)-2-(3-azetidinyl)-3-ethyl-2,6-dihydro-7H-pyrazolo[4,3-d]pyrimidin-7-one trifluoroacetate

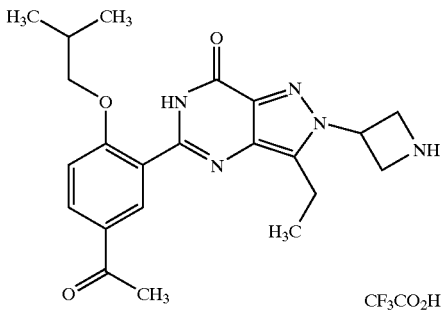

The title compound was obtained as a beige solid, from the protected azetidine from preparation 13, following a similar procedure to that described in preparation 14.

$^1$H NMR (CD$_3$OD, 400 MHz) ☐: 1.01 (d, 6H), 1.30 (t, 3H), 2.1.0 (m, 1H), 2.60 (s, 3H), 3.05 (q, 2H), 4.00 (d, 2H), 4.65 (m, 4H), 5.72 (m, 1H), 7.25 (d, 1H), 8.18 (dd, 1H), 8.38 (d, 1H).

LRMS: m/z (TSP$^+$) 410.1 [MH$^+$]

Preparation 16
4-[(5-Acetyl-2-propoxybenzoyl)amino]-5-ethyl-1H-pyrazole-3–Carboxamide

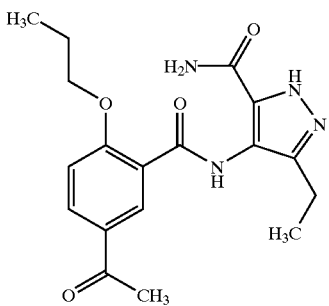

Oxalyl chloride (5.45 ml, 46.4 mmol) was added to a solution of 5-acetyl-2-n-propoxy-benzoic acid (WO 9312095) (11.1 g, 30.9 mmol) in N,N-dimethylformamide (0.1 ml) and dichloromethane (200 ml) under nitrogen at room temperature. Once addition was complete the solution was stirred for 1 hour. The solution was concentrated under reduced pressure and azeotroped with toluene, and the intermediate acid chloride was dissolved in dichloromethane (200 ml). Triethylamine (10.4 ml, 46.4 mmol) was added followed by 4-amino-3-ethyl-1H-pyrazole-5–Carboxamide (WO 9849166) (7.7 g, 30.9 mmol) and the reaction was stirred at room temperature for 16 hours. The mixture was washed with 1N hydrochloric acid (2×100 ml), 10% sodium bicarbonate solution (100 ml) and brine (100 ml), dried over Na$_2$SO$_4$ and the solvent was removed under reduced pressure. The residue was recrystallised from acetonitrile to afford the title compound as a crystalline solid, 14.8 g.

$^1$H NMR (CDCl$_3$, 400 MHz) ☐: 1.06 (t, 3H), 1.27 (t, 3H), 2.03 (m, 2H), 2.62 (s, 3H), 2.95 (m, 2H), 4.29 (t, 2H), 5.43 (br s, 1H), 6.82 (br s, 1H), 7.10 (d, 1H), 8.16 (d, 1H), 8.84 (s, 1H), 10.39 (br s, 2H).

LRMS m/z (TSP$^+$) 359.1 [MH$^+$].

Microanalysis found: C, 60.04; H, 6.18; N, 15.79. C$_{18}$H$_{22}$N$_4$O$_4$ requires C, 60.27; H, 6.18; N, 15.62%.

Preparation 17
5-[(5-Acetyl-2-propoxyphenyl)-3-ethyl-1,6-dihydropyrazolo[4,3-d]pyrimidin-7-one

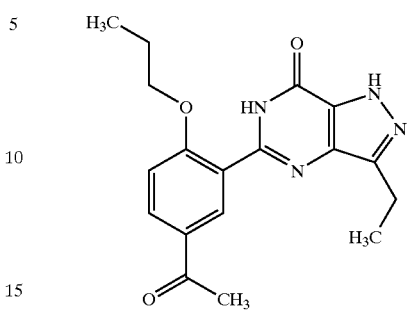

Potassium tert-butoxide (4.37 g, 39 mmol) was added to a solution of the pyrazole carboxamide from preparation 16 (14 g, 39 mmol) in n-propanol (120 ml) and ethyl acetate (10 ml) and the reaction was stirred at reflux for 24 hours. TLC analysis showed starting material remaining, so additional potassium tert-butoxide (4.37 g, 39 mmol) was added and the reaction was stirred at reflux for a further 18 hours.

TLC analysis still showed starting material, so another addition of potassium tert-butoxide (4.37 g, 39 mmol) was made and the reaction was refluxed for a further 70 hours. The solvent was removed under reduced pressure and the residue was partitioned between dichloromethane and water. The organic layer was removed, washed with water (2×), brine, dried over Na$_2$SO$_4$ and concentrated under reduced pressure. The residue was purified by column chromatography on silica gel using dichloromethane:methanol:0.88 ammonia (95:5:0.5) and the product was recrystallised from acetonitrile to afford the title compound as a white solid, 4.94 g.

$^1$H NMR (CDCl$_3$, 400 MHz) ☐: 1.18 (t, 3H), 1.50 (t, 3H), 2.03 (m, 2H), 2.67 (s, 3H), 3.11 (q, 2H), 4.28 (t, 2H), 7.15 (d, 1H), 8.14 (d, 1H), 9.08 (s, 1H), 11.59 (br s, 1H), 11.93 (br s, 1H).

LRMS: m/z (TSP$^+$) 341.3 [MH$^+$].

Microanalysis found: C, 63.18; H, 5.93; N, 12.22. C$_{18}$H$_{20}$N$_4$O$_5$ requires C, 63.51; H, 5.92; N, 16.46%.

Preparation 18
4-[(5-Acetyl-2-propoxybenzoyl)amino]-5-propyl-1-(pyridin-2-yl methyl)-1H-pyrazole-3-carboxamide

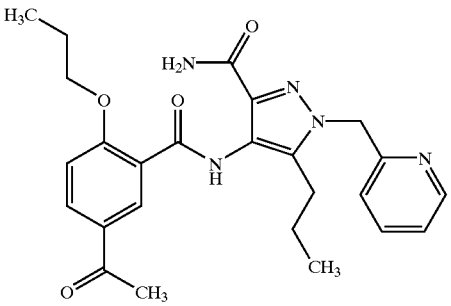

Oxalyl chloride (1.6 ml, 18 mmol) was added to an ice-cooled solution of 5-acetyl-2-n-propoxybenzoic acid (WO 9312095) (2 g, 9 mmol) in N,N-dimethylformamide (0.2 ml) and dichloromethane (200 ml) under nitrogen. Once addition was complete the solution was allowed to warm to room temperature for 3 hours and the solvent was removed under reduced pressure. The intermediate acid chloride was dissolved in pyridine (50 ml) and 4-amino-5-propyl-1-

(pyridin-2-ylmethyl)-1H-pyrazole -3-carboxamide (WO 9954333) (1.5 g, 5.8 mmol) and the reaction was stirred at reflux for 3 hours, then at room temperature for 18 hours. The mixture was partitioned between dilute sodium carbonate solution and dichloromethane, and the organic layer was dried over $Na_2SO_4$ and concentrated under reduced pressure. The residue was purified by column chromatography on silica gel using dichloromethane:methanol (100:0 changing to 98:2 then 92:8) to afford the title compound as a beige solid, 1.5 g.

$^1$H NMR (CDCl$_3$, 400 MHz) □: 0.81 (t, 3H), 1.06 (t, 3H), 1.46 (m, 2H), 2.03 (m, 2H), 2.61 (s, 3H), 2.87 (m, 2H), 4.29 (t, 2H), 5.36 (br s, 1H), 5.47 (s, 2H), 6.70 (br s, 1H), 6.94 (d, 1H), 7.09 (d, 1H), 7.22 (m, 1H), 7.28 (m, 1H), 8.15 (d, 1H), 8.60 (m, 1H), 8.81 (s, 1H), 10.31 (brs, 1H).

LRMS: m/z (TSP$^+$) 464.3 [MH$^+$].

What is claimed is:

1. A compound of formula I:

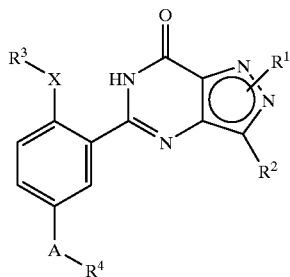

or pharmaceutically or veterinarily acceptable salts, solvates, polymorphs or pro-drugs thereof wherein:

A represents C(O) or CH(OH);

X represents O or NR$^5$;

R$^1$, R$^3$, R$^4$ and R$^5$ independently represent H, C$_1$–C$_6$ alkyl, Het, C$_1$–C$_6$ alkylHet, aryl or C$_1$–C$_6$ alkylaryl (which latter five groups may all be optionally substituted and/or terminated with one or more substituents selected from halo, cyano, nitro, OR$^6$, OC(O)R$^6$, C(O)R$^8$, C(O)OR$^6$, NR$^6$C(O)NR$^7$R$^8$, NR$^6$C(O)OR$^8$, OC(O)NR$^7$R$^8$, C(O)NR$^9$R$^{10}$, NR$^9$R$^{10}$, SO$_2$NR$^9$R$^{10}$, SO$_2$R$^{11}$, C$_1$–C$_6$alkyl, Het, C$_1$–C$_6$ alkytHet, aryl or C$_1$–C$_6$ alkylaryl wherein said latter five substituent and/or terminal groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$); or when X represents NR$^5$ then R$^3$ and R$^5$ together with the nitrogen atom to which they are bound can form a heterocyclic ring which is optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^2$ represents H, halo, cyano, nitro, OR$^6$, OO(O)R$^6$, C(O)R C(O)OR$^6$, NR$^6$C(O)NR$^7$R$^8$, NR$^6$C(O)OR, OO(O)NR$^7$R$^8$, C(O)NR$^9$R$^{10}$, NR$^9$R$^{10}$, SO$_2$NR$^9$R$^{10}$, SO$_2$R$^{11}$, C$_1$–C$_6$ alkyl, Het, C$_1$–C$_6$ alkylHet, aryl or C$_1$–C$_6$ alkylaryl (which latter five groups may all be optionally substituted and/or terminated with one or more substituents selected from halo, cyano, nitro, OR$^6$, OC(O)R$^6$, C(O)R$^6$, C(O)OR$^6$, NR$^6$C(O)NR$^7$R, NR$^6$C(O)OR$^6$, OC(O)NR$^7$R$^8$, C(O)NR$^9$R$^{10}$, NR$^9$R$^{10}$, SO$_2$NR$^9$R$^{10}$, SO$_2$R$^{1'}$, C,-06 alkyl, Het, C$_1$–C$_6$ alkylHet, aryl or C$_1$–C$_6$ alkylaryl wherein said latter five substituent and/or terminal groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$);

R$^6$ represents H, C$_1$–C$_6$ alkyl, Het, C,-Ce alkyiHet, aryl or 01–06 alkylaryl (which latter five groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$);

R$^7$ and R$^8$ independently represent H, C$_1$–C$_6$ alkyl, Het, C$_1$–C$_6$ alkylHet, aryl or C$_1$–C$_6$ alkylaryl (which latter five groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$); or R$^7$ and R$^8$ together with the nitrogen atom to which they are bound can form a heterocyclic ring;

R$^9$ and R$^{10}$ independently represent H, C(O)R$^6$, SO$_2$R$^{11}$, C$_1$–C$_6$ alkyl, Het, C$_1$–C$_6$ alkylHet, aryl or C$_1$–C$_6$ alkylaryl (which latter five groups are all optionally substituted and/or terminated with one or more substituents selected from halo, cyano, nitro, OR$^{12}$, OC(O) R$^{12}$, C(O)R$^{12}$, C(O)OR$^{12}$, NR$^{12}$C(O)NR$^{13}$R$^{14}$, NR$^{12}$C (O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$); or R$^9$ and R$^{10}$ together with the nitrogen atom to which they are bound can form a heterocyclic ring;

wherein when R$^7$ and R$^8$, or R$^9$ and R$^{10}$ together with the nitrogen atom to which they are bound form a heterocyclic ring, said heterocyclic ring is optionally substituted and/or terminated with one or more substituents selected from: halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O) OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^{11}$ represents a C$_1$–C$_6$ alkyl, Het, C$_1$–C$_6$ alkylHet, aryl or C$_1$–C$_6$ alkylaryl group is optionally substituted and/or terminated with one or more substituents selected from halo, cyano, nitro, OR$^{12}$, OC(O)R$^{12}$, C(O)R$^{12}$, C(O) OR$^{12}$, NR$^{12}$C(O)NR$^{13}$R$^{14}$, NR$^{12}$C(O)OR$^{12}$, OC(O) NR$^{13}$R$^{14}$, C(O)NR$^{15}$R$^{18}$, NR$^{15}$R$^{16}$, SO$_2$NR$^{15}$R$^{16}$, SO$_2$R$^{17}$;

R$^{12}$ represents H or C$_1$–C$_6$ alkyl;

R$^{13}$ and R$^{14}$ independently represent H or C$_1$–C$_6$ alkyl; or R$^{13}$ and R$^{14}$ together with the nitrogen atom to which they are bound can form a heterocyclic ring;

R$^{15}$ and R$^{16}$ independently represent H, C(O)R$^{12}$, SO$_2$R$^{17}$ or C$_1$–C$_6$ alkyl; or R$^{15}$ and R$^{16}$ together with the nitrogen atom to which they are bound can form a heterocyclic ring;

R$^{17}$ represents C$_1$–C$_6$ alkyl;

Het represents an optionally substituted four- to twelve-membered heterocyclic group, which group contains one or more heteroatoms selected from nitrogen, oxygen, sulpur and mixtures thereof;

with the proviso that when X represents O and R$^1$ represents H, C$_3$–C$_1$ alkyl optionally substituted with fluoro or C$_3$–C$_5$ cycloalkyl then $R^2$ does not represent H, $C_1$–$C_6$ alkyl optionally substituted with one or more fluoro substituents or with $C_3$–$C_6$ cycloalkyl; or $R^3$ does not represent $C_1$–$C_6$ alkyl optionally substituted with one or morfluoro substituents or with $C_3$–$C_6$ cycloalkyl; $C_3$–$C_5$ cycloalkyl; $C_3$–$C_6$ alkenyl; or $C_3$–$C_6$ alkynyl; or $R_4$ does not represent $C_1$–$C_4$ alkyl optionally substituted with OH, $NR^9R^{10}$, CN, $CONR^9R^{10}$, $SO_2NR^9R^{10}$ or $CO_2R^6$ wherein $R^6$ is H or $C_1$–$C_4$ alkyl and $R^9$ and $R^{10}$ are each independently H or $C_1$–$C_4$ alkyl, or together with the nitrogen atom to which they are attached form a pyrrolidinyl, piperidino, morpholino, 4-substituted piperizinyl or imidazolyl group wherein said group is optionally substituted with $C_1$–$C_4$ alkyl or OH; $C_2$–$C_4$ alkenyl optionally substituted with CN, $CONR^9R^{10}$ or $CO_2R^6$; $C_2$–$C_4$ alkanoyl optionally substituted with $NR^9R^{10}$; $(C_2$–$C_4)OH$ optionally substitued with $NR^9R^{10}$; $(C_2$–$C_3)$alkoxy$(C_1$–$C_2)$alkyl optionally substituted with OH or $NR^9R^{10}$.

2. A compound as defined in claim 1 wherein:

X represents O;

A represents C(O) or CH(OH);

$R^1$ represents $C_1$–$C_6$ alkyl substituted and/or terminated with $OR^6$, $C(O)OR^6$, $C(O)NR^9R^{10}$ or $NR^9R^{10}$ wherein said latter four groups are optionally substituted and/or terminated as defined hereinbefore; or $R^1$ represents Het, $C_1$–$C_6$ alkylHet, aryl or $C_1$–$C_6$ alkylaryl optionally substituted and/or terminated with one or more substituents selected from halo, $C_1$–$C_6$ alkyl, $OR^6$, $C(O)OR^6$, $C(O)NR^9R^{10}$ and $NR^9R^{10}$ wherein said latter five groups are optionally substituted and/or terminated as defined hereinbefore;

$R^2$ and $R^3$ independently represent Cs-Ce alkyl, Het, $C_1$–$C_6$ alkylHet, aryl or $C_1$–$C_6$ alkylaryl optionally substituted and/or terminated with one or more substituents selected from halo, $OR^6$, $C(O)OR^6$ and $NR^9R^{10}$ wherein said latter three groups are optionally substituted and/or terminated as defined hereinbefore;

$R^4$ represents $C_1$–$C_6$ alkyl, Het, $C_1$–$C_6$ alkylHet, aryl or $C_1$–$C_6$ alkylaryl optionally substituted and/or terminated with one or more substituents selected from halo and $OR^6$ wherein said $OR^6$ group is optionally substituted and/or terminated as defined hereinbefore;

wherein $R^6$, $R^9$ and $R^{10}$ are as hereinbefore defined.

3. A compound as defined in claim 1 wherein:

A represents C(O) and X represents O;

$R^1$ represents $C^1$–$C^6$ alkyl optionally substituted and/or terminated with one or more substituent groups selected from $OR^6$, $C(O)OR^6$ and $C(O)NR^9R^{10}$; or $R^1$ represents Het or $C_1$–$C_6$ alkylHet optionally substituted and/or terminated with one or more substituent groups selected from $C_1$–$C_6$ alkyl, $OR^6$, $C(O)OR^6$ and $C(O)NR^9R^{10}$;

$R^2$ represents $C_1$–$C_6$ alkyl optionally substituted and/or terminated with one or more substituent groups selected from halo and $OR^6$;

$R^3$ represents $C_1$–$C_8$ alkyl optionally substituted and/or terminated with one or more substituents selected from halo and $OR^6$;

$R^4$ represents $C_1$–$C_6$ alkyl optionally substituted and/or terminated with one or more substituents selected from halo and $OR^4$;

wherein $R^6$, $R^9$ and $R^{10}$ are as hereinbefore defined.

4. A compound as defined in claim 1 wherein:

A represents C(O) and X represents O;

$R^1$ represents $C_1$–$C_4$ alkyl, an azetidinyl group substituted and/or terminated with one or more substituent groups selected from $C_3$–$C_4$ alkyl, $OR^6$, $C(O)OR^6$ and $C(O)NR^9R^{10}$; or $R^1$ represents a $(C_1$–$C_6)$pyridinyl group which may be optionally substuted with one or more substituent groups selected from $C_3$–$C_4$ alkyl, $OR^6$, $C(O)OR^6$ and $C(O)NR^9R^{10}$;

$R^2$ represents $C_1$–$C_3$ alkyl optionally substituted and/or terminated with one or more substituent groups selected from halo and $OR^6$;

$R^3$ represents $C_1$–$C_4$ alkyl optionally substituted and/or terminated with one or more substituents selected from halo and $OR^6$;

$R^4$ represents $C_1$–$C_3$ alkyl optionally substituted and/or terminated with one or more substituents selected from halo and $OR^6$;

wherein $R^6$ is H or a $C_1$–$C_4$ alkyl group and wherein $R^9$ and $R^{10}$ are independently selected from methyl or ethyl groups.

5. A compound according to claim 1 wherein:

A represents C(O) and X represents O;

$R^1$ represents $C_2$–$C_3$ alkyl group substituted and/or terminated with one or more substituent groups selected from $OR^6$ or $C(O)OR^6$;

$R^2$ represents $C_2$–$C_3$ alkyl, and is preferably ethyl, optionally substituted and/or terminated with one or more substituent groups selected from halo and $OR^6$;

$R^3$ represents $C_3$–$C_4$ alkyl, and is preferably propyl, optionally substituted and/or terminated with one or more substituents selected from halo and $OR^6$;

$R^4$ represents $C_1$–$C_2$ alkyl, and is preferably ethyl, optionally substituted and/or terminated with one or more substituents selected from halo and $OR^8$;

wherein $R^6$ is H or a $C_2$–$C_4$ alkyl group.

6. A formulation comprising a compound as defined in claim 1 in admixture with a pharmaceutically or veterinarily acceptable adjuvant, diluent or carrier.

7. A method of treating male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) by administering a therapeutically effective amount of a compound of claim 1.

* * * * *